(12) United States Patent
Palmer et al.

(10) Patent No.: US 6,583,167 B2
(45) Date of Patent: Jun. 24, 2003

(54) METHODS AND KITS FOR TREATING AND DIAGNOSING LEIOMYOMAS

(75) Inventors: Stephen S. Palmer, Stockton, NJ (US); Romana A. Nowak, West Roxbury, MA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/741,652

(22) Filed: Dec. 20, 2000

(65) Prior Publication Data

US 2001/0002393 A1 May 31, 2001

Related U.S. Application Data

(63) Continuation of application No. 09/044,046, filed on Mar. 18, 1998, now abandoned.
(60) Provisional application No. 60/041,261, filed on Mar. 18, 1997.

(51) Int. Cl.$^7$ .............................................. A61K 31/415
(52) U.S. Cl. ........................................ 514/400; 514/399
(58) Field of Search .................................. 514/399, 400

(56) References Cited

FOREIGN PATENT DOCUMENTS

| WO | WO 92/09701 | 6/1992 |
| WO | WO 94/04190 | 3/1994 |
| WO | WO 94/04190 A1 * | 3/1994 |

OTHER PUBLICATIONS

Rodgers et al., J. Clin. Invest., vol. 94, Sep. 1994, pp. 946–953.*
Schatz et al., Journal of Clinical Endorinology and Metabolism, vol. 78, No. 6, 1994.*
Nagase, H., Human Stromelysins 1 and 2. In. Methods Enzymol. 248:449–470. Ed. Alan J. Barret, Academic Press, Inc. New York, NY, 1995.*
Stedman's Online Medical Dictionary for the terms leiomyoma, tumor and fibroleiomyoma, 2002.*
Norris, H.J, and Zaloudek, C.J., 1977. Mesenchymal Tumors of the Uterus. In: Pathology of the Female Genital Tract; pp. 352–392. Blaustein A., ed. Springer Verlag, New York, NY.
Friedman A..J., Barbieri R.L., Benacerraf B.R., and Schiff I.,, 1987. Treatment of Leiomyomata with Intranasal or Subcutaneous Leuprolide, a gonadotropin–releasing hormone agonist. Fert. Steril. 48: 560–565.
Friedman A.J., Hoffman D.I., Comite F., Browneller, R.W., Miller J.D., 1991. Treatment of Leiomyomata Uteri with Leuprolide Acetate Depot: A double blind, placebo–controlled, multicenter study. Obstet. Gynecol.. 77: 720–725.

Andreyko, J.L., Blumenfeld Z., Marshall L.A., Monroe S.E., Hricak H. and Jaffe R.B., 1988. Use of an Agonistic Analog of Gonadrotropin–Relating Hormone (nafarelin) to Treat Leiomyomas; Assessment by Magnetic Resonance Imaging. A. J. Obstet. Gynecol. 158: 903–910.

Murphy, A.A., Kettel, L.M., Morales A.J., , Roberts V.J. and Yen S.C., 1993. Regression of Uterine Leiomyomata in Response to the Antiprogesterone RU–486. J. Clin. Endocrinol. Metab. 76: 513–517.

Townsend, D.E., Sparkes R.S., Baluda, M.C., and McClelland G., 1970. Unicellular Histogenesis of Uterine Leiomyomas as Determined by Electrophoresis of Glucose–6–Phopshate Dehydrogenase. Am. J. Obstet. Gynecol. 207:1168–1173.

Vogelstein, B., Fearon E.R., Hamilton, S.R., and Feiberg, A.P., 1985. Use of Restriction Fragment Length Polymorphisms to Determine the Clonal Origin of Human Tumors. Science 227: 642–645.

Hasimoto K., Azuma C., Kamiura S. Kimura T., Nobunaga T., Kanai T., Sawada M., Noguchi S., Saji F., 1995. Clonal Determination of Uterine Leiomyomas by Analzing Differential Inactivation of the X–chromosome–linked phosphoglycerokinase gene. Gynecol. Bostet. Invest. 40: 204–208.

Felmingham, J.E., and Corcoran R., 1975. Comment: Rapid Enlargement of a Uterine Fibroid After Clomiphene Therapy. Brit. J. Obstet. Gynaecol. 82: 431–432.

Dilts, P.V. Jr., Hopkins, M.P., Chang, A.E., and Cody, R.L., 1992. Rapid Growth of Leiomyoma in Patient Receiving Tamoxifen. Am. J. Obstet. Gynecol. 166: 167–168.

Puistola U., Risteli, L., RisteliJ. and Kauppila, A., 1990. Collagen Metabolism in Gynecologic Patients: Changes in the Concentration of the Aminoterminal Propeptide of Type III Procollagen in Serum. Am. J. Obstet. Gynecol. 163: 1276–1281.

Rodgers, W.H., Osteen, K.G., Matrisian, L.M., Navre, M., Guidice, L.C., and Gorstein F., 1993, Expression and localization of Matrilysin, a Matrix Metalloproteinase, in Human Endometrium during the Reproductive Cycle. A.m. J. Obstet. Gynecol. 168: 253–260.

(List continued on next page.)

*Primary Examiner*—Dwayne C. Jones
(74) *Attorney, Agent, or Firm*—Myra McCormack

(57) ABSTRACT

This invention provides methods of treating a subject suffering from a leiomyoma which comprise administering to the subject a therapeutically effective amount of an agent, or alternatively a plurality of agents, which inhibit specific metalloproteinases. This invention further provides diagnostic methods of determining whether a tumor in a subject is a leiomyoma. This invention further provides pharmaceutical compositions and kits for practicing the instant methods. Finally, this invention provides a method of determining whether an agent specifically inhibits certain metalloproteinases.

18 Claims, 15 Drawing Sheets

OTHER PUBLICATIONS

Rodgers, W.H., Matrisian, L.M., Guidice, L.C., Dsupin B., Cannon, P., Svitek C., Gorstein, F. and Osteen K.G., 1994. Patterns of Matrix Metalloproteinase Expression in Cycling Endometrium Imply Differential Functions and Regulation by Steroid Hormones. J. Clin. Invest. 94: 946–953.

Schatz F., Papp, C., Toth–Pal, E. and Lockwood, C.J., 1994, Ovarian Steroid–Modulated Stromelysin–1 Expression in Human Endometrial Stromal and Decidual Cells. J. Clin. Endocrinol. Metab. 78: 1467–1472.

Harrison–Woolrych, M. and Robinson, R., 1995. Fibroid Growth Response to High–Dose Progrestogen. Fert. Steril. 64: 191–192.

Murphy, A.A., Moales A.J., Kettel, L.M., and Yen S.S.C., 1995. Regression of Uterine Leiomyomata to the Antiprogesterone RU486: dose–response effect. Fertil. Steril. 64: 187–190.

MacNaul, K.L., Chartrain, N., Lark M., Tocci, M.J., and Hutchinson, N.I., 1990. Discoordinate Expression of Stromelysin, Collagenase, and Tissue Inhibitor of Metalloproteinases–1 in Rheumatoid Human Synovia Fibroblasts. J. Biol. Chem. 265: 17283–17245.

Hembry, R.M., Bbagga, M.R., Reynolds, J.J. and Hamblen, D.L., 1995. Immunolocalization Studies on Six Matrix Metalloproteinases and their Inhibitors, TIMP–1 and TIMP–2, in Synovia from Patients with Osteo–and Rheumatoid Arthritis. Ann. Rheum. Dis. 54: 25–32.

Declerck, Y.A., Yean, T.D., Chan, D., Shimada, H., Langley, K.E., 1991. Inhibition of Tumor Invasion of Smooth Muscle Cell Layers by Recombinant Human Metalloproteinase Inhibitor. Cancer Res. 52: 2151–2157.

Declerck, Y.A., Perez, N., Shimada H., Boone T.C., Langley, K.E., Taylor, S.M., 1992. Inhibition of Invasion and Metastasis in Cells Transfected with an Inhibitor of Metalloproteinases. Cancer Res. 52: 701–708.

Stearns, M.E., Wang, M., Stearns, M., 1995. IL–10 blocks Collagen IV Invasion by "invasion stimulating factor" activated PC–3 ML Cells; upregulation of TIMP–1 Expression. Oncol. Res. 7: 157–163.

Hampton, A.L., and Salamonsen, L.A., 1994. Expression of Messenger Ribonucleic Acid Encoding Matrix Metalloproteinases and their Tissue Inhibitors is Related to Menstruation. J. Endocrinol. 141: R1–R3.

Chirgwin, J.M., Przbyla, A.E., MacDonald, R.J., Rutter, W.J., 1979. Isolation of Biologically active Ribonucleic Acid From Sources Enriched in Ribonucleases. Biochem. 18: 5294–5300.

Nowak, R.A., Rein, M.S., Heffner, L.J., Friedman, A.J., and Tashjian, A.H., Jr. 1993. Production of Prolactin by Smooth Muscle Cells Cultured from Human Uterine Fibroid Tumors. J. Clin. Endocrinol. Metab. 76: 1308–1313.

Nuovo, G.J., MacConnell, P.B., Simsir, A, Valea, F. and French., D.L., 1995. Correlation of the in situ detection of polymerase chain reaction–amplified metalloproteinase complementary DNA's and their inhibiotrs with prognosis in cervical carcinoma. Cancer Research 55: 267–275.

Harrison–Woolrych, M.L., Charnock–Jones, D.S. and Smith, S.K., 1994. Quantification of Messenger Ribonucleic Acid For Epidermal Growth Factor in Human Myometrium and Leiomyomata Using Reverse Transcriptase Polymerase Chain Reaction. J. Clin. Endocrinol. Metab. 78: 1179–1184.

Anderson, J., Grine, E.A., Eng. C.L–Y, Zhao, K., Barbieri, R.L., Chumas, J. and Brink, P. Expression of Connexin–43 in Human Myometrium and Leiomyomas. A.m. J. Obstet. Gynecol. 169: 1266–1276, 1993.

Liotta, L.A., and Stetler–Stevenson, W.G., 1991. Tumor Invasion and Metastasis: An Imbalance of Positive and Negative Regulation. Cancer Research 51: 5054s–5059s.

Kato, N., Nawa, A., Tamakoshi, K., Kikkawa, F., Suganuma, N., Okamoto, T., Goto, S., Tomoda, Y., Hamaguchi, M., and Nakajima,, M., 1995. Suppression of Gelantinase Production with Decreased Invasiveness of Choriocarcinoma Cells by Recombinant Interferon Beta. Am. J. Obstet. Gynecol. 172: 601–606.

Rao, J.S., Yamamoto,M., Mohaman, S., Gokaslan, Z.L., Fuller, G.N., Stetler–Stevenson, W.G., Rao, V.H., Liotta, L.A., Nocolson, G.L., and Sawaya, R.E., 1995. Expression and localization of 92 kDa Type IV collagnease/gelatinase B. (MMP–9) in Human Gliomas. Clin. Exp. Metastasis 14: 12–18.

Okada, Y., Gonoji, Y., Naka, K., Tomita, K., Nakanishi, I., Iwata, K., Yamashita, K. and Hayakawa, T., 1992. Matrix Metalloproteinase 9 (92–kDa gelatinase/type IV collagenase) from HT 1080 Fibrosarcoma cells. J. Biol. Chem. 267: 21712–21719.

Imai, K., Yokohama, Y., Nakanishi, I., Ohuchi, E., Fjuii, Y., Nakai, N., and Okada, Y., 1995. Matrix metalloproteinase 7 (matrilysin) from human rectal carcinoma cells, J. Biol. Chem. 270: 6691–6697.

Witty, J.P., McDonnell, S., Newell, K.J., Cannon P., Navre, M., Tressler, R.J. and Matrisian, L.M., 1994. Modulation of Matrilysin levels in Colon Carcinoma Cell Lines Affects Tumorigenicity in vivo. Cancer Res. 54: 4805–4812.

Yamamoto, H., Itoh F., Hinoda Y., and Imai K., 1995. Suppression of Matrilysin Inhibits Colon Cancer Cell Invasion in vitro. Int. J. Cancer 61: 218–222.

McDonnell, S., Navre, N., Coffey R.J., and Matrisian, L.M., 1991. Expression and localization of the matrix metalloproteinase Pump–1 (MMP–7) in human gastric and colon carcinomas. Molec. Carcinog. 4: 527–533.

Bassett, P., Bellocq, J.P., Wolf, C., Stoll, I., Hutin, P., Limacher, J.M., Podhajcer, Chenard M.P., Rio M.C. and Chambpon, P., 1990. A novel metalloproteinase gene specifically expressed in stromal cells of breast carcinomas. Nature 348: 699–704.

Wolf, C., Rouyer, N., Lutz, Y., Adida, C., Loriot, M., Bellocq, J.P., Chambon, P., and Basset, P., 1993. Stromelysin–3 belongs to a subgroup of proteinases expressed in breast carcinoma fibroblastic cells in possibly implicated in tumor progression. Proc. Natl. Acad. Sci. USA 90: 1843–1847.

Salamonsen, L.A., 1996. Matrix metalloproteinases and their tissue inhibitors in endocrinology. Trends in Endocrinol. Metab. 7:28–34.

Cockett, M.I., Birch, M.L., Murphy, G., Hart, I.R., and Docherty A.J.P., 1994. Metalloproteinase domain structure, cellular invasion and metastasis. Bioch. Soc. Transact. 22: 55–57.

McDonnell, S., Wright, J.H., Gaire, M.M and Matrisian., L.M., 1994. Expression and regulation of stromelysin and matrilysin by growth factors and oncogenes. Bioch. Soc. Transact. 22: 58–63.

Rucklidge, G.J., Edvardsen, K., and Bock., E., 1994. Cell–adhesion molecules and metalloproteinases: a linked role in tumor cell invasiveness. Bioch. Soc. Transact. 22: 63–68.

Nagase, H., 1995. Human Stromelysins 1 and 2. In: Methods Enzymol. 248: 449–470. Ed. Alan J. Barret, Academic Press, Inc., New York, NY.

Pei, D., Majmudar, G., and Weiss, S.J., 1994. Hydrolytic inactivation of a breast carcinoma cell–derived serpin by human stromelysin–3. J. Biol. Chem. 269: 25849–25855.

Sires, U.I., Murphy, G., Baragi, V.M., Fliszar, C.J., Welgus, H.G., and Senior R.M., 1994. Matrilysin is much more efficient than other matrix metalloproteinases in the proteolytic inactivation of α1–antitrypsin. Bioc. Biophys. Res. Comm. 204: 613–620.

Von Bredow, D. C., Nagle, R.B., Bowden, G.T., Cress, A.E., 1995. Degradation of fibronectin fibrils by matrilysin and characterization of the degradation products. Exp. Cell. Res. 221: 83–91.

Wilson, C.L., Matrisian, L. M., 1996. Matrilysin: an epithelial matrix metalloproteinase with potentially novel functions. Int. J. Biochem. Cell Biol. 28: 123–136.

Unden, A. B., Sandstedt, B., Bruce, K., Hedblad M.–A. and Shahle–Backdahl,. M.–S, 1996. Stromelysin–3 mRNA associated with myofibroblasts is overexpressed in aggressive basal cell carcinoma and in dermatfibroma but not in dermatofibrosarcoma. J. Invest. Dermatol. 107: 147–153.

Jeziorsak, M., Salamonsen, L.A., and Woolley, D.E., 1995. Mast cell and eosinophil distribution and activation in human endometrium throughout the menstrual cycle. Biol. Reprod. 53: 312–320.

Busiek, D.F., Ross, F.P., McDonnell, S., Murphy, G., Matrisian, M., Welgus, H.G., 1992. The matrix metalloportease matrilysin (PUMP) is expressed in developing human mononuclear phagocytes. J. Biol. Chem. 267: 9087–9092.

Malik, N., Greenfield, B.W., Wahl, A.F., and Kiener, P.A., 1996. Activation of human monocytes through CD40 induces matrix metalloproteinases. J. Immunol. 156: 3952–3960.

Lee E., Grodzinsky A.J., Libby P., Clinton S.K., Lark M.W., Lee R.T., 1995. Human vascular smooth muscle cell–monocyte interactions and metalloproteinase secretion in culture. Arterioscler. Thromb. Vasc. Biol. 15: 2284–2289.

Corcoran, M.L., Kibbey M.C., Kleinman H.K., Wahl L.M., 1995. Laminin SIKVAV peptide induction of monocyte/macrophage prostaglandin E2 and matrix metalloproteinases. J. Biol. Chem. 270: 10365–10368.

Maillard J.L., Favreau C., Reboud–Ravaux M., 1995. Role of monocyte/macrophage derived matrix metalloproteinases (gelatinases) in prolonged skin inflammation. clin. Chim. Acta 233: 61–74.

Lacraz S., Isler P., Vey E., Welgus H.G., Dayer, J.–M., 1994. Direct contact between T lymphocytes and monocytes is a major pathway for induction of metalloproteinase expression. J. Biol. Chem. 269: 22027–22033.

Hennig Y., Wanschura S., Deichert U., Bartnitzke S., Bullerdiek J., 1996. Rearrangements of the high mobility group protein family genes and the molecular genetic origin of uterine leiomyomas and endometrial polyps. Mol. Hum. Reprod. 2: 277–283.

Fejzo, M.S., Yoon S.–J., Montgomery K., Rein M.S., Weremowicz S., Krauter K.S., Dorman T.E., Fletcher J.A., Mao J., Moir D.T., Kucherlapati R.S. and Morton C.C., 1995. Identification of a YAC spanning the translocation breakpoints in uterine leiomyomata, pulmonary chondroid hamartoma and lipoma: physical mapping of the 12q14–q15 breakpoint region in uterine leiomyomata. Genomics 26: 265–271.

Osteen K.G., Rodgers W.H., Gaire M., Hargrove J.T., Gorstein F. and Matirisian L.M., 1994. Stromal–epithelial interaction mediates steroidal regulation of metallo–proteinase expression in human endometrium. Proc. Natl. Acad. Sci. USA 91: 10129–10133.

Osteen K.G., Bruner K.L., Sierra–Rivera E., Keller N.R., Eisenberg E., 1996. Interleukin 1a opposes progesterone suppression of matrix metalloproteinases in an endometriosis model. Biol. Reprod. 54 (Suppl): 259.

Brooks, P.C., Stromblad S., Sanders L.C., Von Schalscha T.L., Aimes R.T., Stetler–Stevenson W.G., Quigley J.P., Cheresh S.A., 1996. Localization of matrix metalloproteinase MMP–2 to the surface of invasive cells by interaction with integrin avb3. Cell 85: 683–693.

Xia M., Sreedharan S.P., Dazin P., Damsky C.H., Goetzel E.J., 1996. Integrin–dependent role of human T cell matrix metalloproteinase activity in chemotaxis through a model basement membrane. J. Cell. Biochem. 61: 452–458.

Gaire M., Magbanua Z., McDonnell, McNeil L., Lovett and Matrisian L.M., 1994. Structure and expression of the human gene for the matrix metalloproteinase matrilysin. J. Biol. Chem. 269: 2032–2040.

Hara T., Tanaka S., Sato H., Seiki M., Tojo H., Tachi C., 1995. Expression of matrix metalloproteinase–11 (stromelysin–3) and TIMP–1 genes in the placenta and the uterus during estrous cycles and gestation in the mouse. J. Reprod. Dev. 41: 287–292.

Hosono T., Ito A., Sato T., Nagase H., and Mori Y., 1996. Translational augmentation of pro–matrix metalloproteinase 3 (prostromelysin–1) and tissue inhibitor of metalloproteinases (TIMP)–1 mRNAs induced by epidermal growth factor in human uterine cervical fibroblasts. FEBS Lett. 381: 115–118.

Reponen P., Leivo I., Sahlberg C., Apte S.S., Olsen B.R., Thesleff I. and Tryggvason K., 1995. 92–kDa type IV collagenase and TIMP–3, but not 72–kDa type IV collagenase or TIMP–1 or TIMP–2, are highly expressed during mouse embryo implantation. Dev. Dyn. 202: 388–396.

Strongin A.Y., Marmer B.L., Grant G.A. and Goldberg G.I., 1993. Plasma membrane–dependent activation of the 72–kDa Type IV collagenase is prevented by complex formation with TIMP–2. J. Biol. Chem. 268: 14033–14039.

Cawston T.E., Murphy G., Mercer E., Galloway W.A., Hazelman B.L., and Reynolds J.J., 1983. The interaction of purified rabbit bone collagenase with purified rabbit bone metalloproteinase inhibitor. Biochem J. 211: 313–318.

Murphy G., Koklitis P. and Carne A.F., 1989. Dissociation of tissue inhibitor of metalloproteinases (TIMP) from enzyme complexes yields fully active inhibitor. Biochem. J. 261: 1031–1034.

Imren S., Kohn D.B., Shimada H., Blavier L., Declerck Y.A., 1996. Overexpression of tissue inhibitor of metalloproteinases–2 by retroviral–mediated gene transfer in vivo inhibits tumor growth and invasion. cancer Res. 56: 2891–2895.

Grignon D.J., Sakr W., Toth M., Ravery V., Angulo J., Shamsa F., Pontes J.E., Crissman J.C., Fridman, R., 1996. High levels of tissue inhibitor of metalloproteinase–2 (TIMP) expression are associated with poor outcome in invasive bladder cancer. Cancer Res. 56: 1654–1659.

Zeng Z.-S., Cohen A.M., Zhang Z.-F., Stetler-Stevenson W., Guillem J.G., 1995. Elevated tissue inhibitor of metalloproteinase 1 RNA in colorectal cancer stroma correlates with lymph node and distant metastases. Clin. Cancer Res. 1: 899–906.

Visscher D.W., Hoyhtya M., Ottosen S.K., Liang C.-M., Sarkar F.H., Crissman J.D., Fridman R., 1994. Enhanced expression of tissue inhibitor of metalloproteinase-2 (TIMP-2) in the stroma of breast carcinomas correlates with tumor recurrence. Int. J. Cancer 59: 339–344.

Dean D.D., Martel-Pelletier J., Pelletier J.P., Howell D.S. and Woessner J.F., Jr., 1989. Evidence for metalloproteinase and metalloproteinase inhibiot imbalance in human osteoarthritic cartilage. J. Clin. Invest. 84: 678–685.

McGuire M.B., Murphy G., Reynolds J.J. and Russell R.G.G., 1981. Production of collagenase and inhibiotr (TIMP) by normal, rheumatoid, and osteoarthritic synovium in vitro: effects of hydrocortisone and indomethacin. Clin. Sci. 61: 703–710.

Ignar-Trowbridge D.M., Nelson K.G., Bidwell M.C., Curtis S.W., Washburn T.F., McLachlan J.A and Korach K.S., 1992. Coupling of dual signaling pathways: epidermal growth factor action involves the estrogen receptor. Proc. Natl. Acad. Sci. U.S.A. 89: 4658–4662.

Ignar-Trowbridge D.M., Teng C.T., Ross K.A., Parker M.G., Korach K.S. and McLachlan J.A., 1993 Peptide growth factors elicit estrogen receptor-dependent transcriptional activation of an estrogen-responsive element. Mol. Endocrinol. 7: 992–998.

Ignar-Trowbridge D.M., Pimentel M., Parker M.G., McLachlan J.A., Korach, K.S., 1996. Peptide growth factor cross-talk with the estrogen receptor requires the A/B domain and occurs independently of protein kinase C or estradiol. Endocrinol 137: 1735–1744.

Tiltman A., 1985. The effect of progestins on the mitotic activity of uterine fibromas. Int. J. Gynecol. Pathol 4: 89–96.

Kawagucki K., Fuji S., Konishi I., Nanbu Y., Nonogake H., Mori T., 1989. Mitotic activity in uterine leiomyomas during the menstrual cycle. Am. J. Obstet. Gynecol. 160: 637–641.

Mangrulkar R.S., Ono M., Ishikawa M., Takashima S., Klagsbrun M., Nowak R.A., 1995. Isolation and characterization of heparin-binding growth factors in human leiomyomas and normal myometrium. Biol. Reprod. 53: 636–46.

Knight C.G., Willebrock F., Murphy G., 1992. A novel coumarin-labelled peptide for sensitive continuous assays of the matrix metalloproteinases. FEBS 296, No. 3: 263–266.

Dou et al., 1997, Differential expression of matrix metalloproteinases and their tissue inhibitors in leiomyomata: a mechanism for gonadotrophin releasing hormone agonist-Induced tumour regression. Molecular Human Reproduction. vol. 3, No. 11:1005–1014.

* cited by examiner

← 2.9 kb Collagenase

← 1.2 kb Tubulin

← 2.3 kb Stromelysin

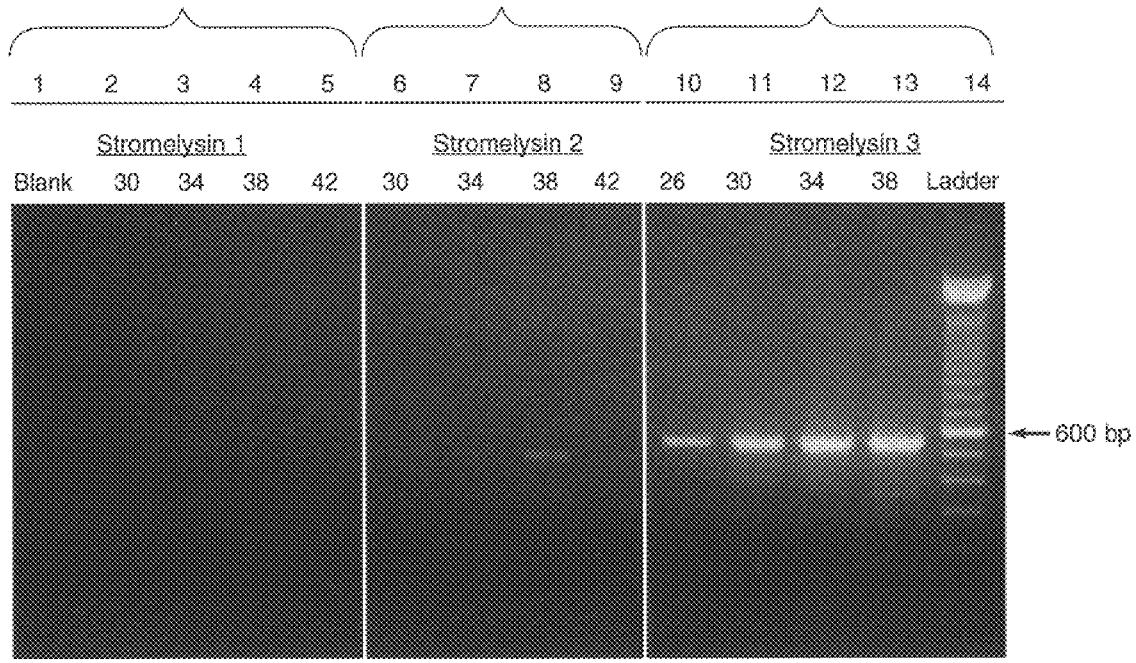

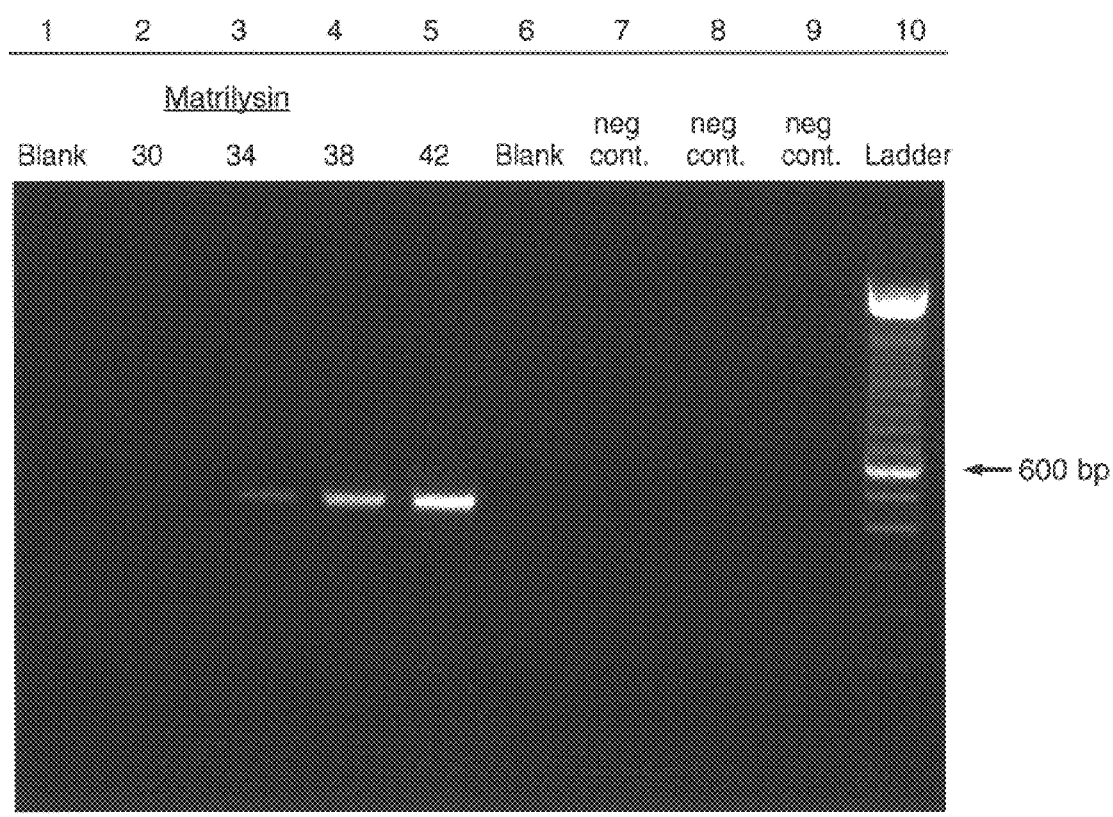

FIG. 3A ENZYME
Predicted Restriction Digest Analysis of Stromelysin 1, Stromelysin 2, Stromenlysin 3 and Matrilysin PCR products
Stromelysin 1
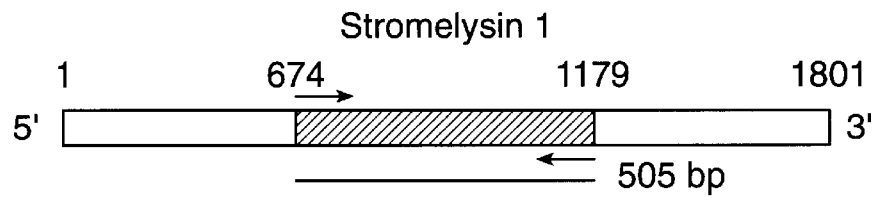
Hind III      68, 264, 173
Stromelysin 2
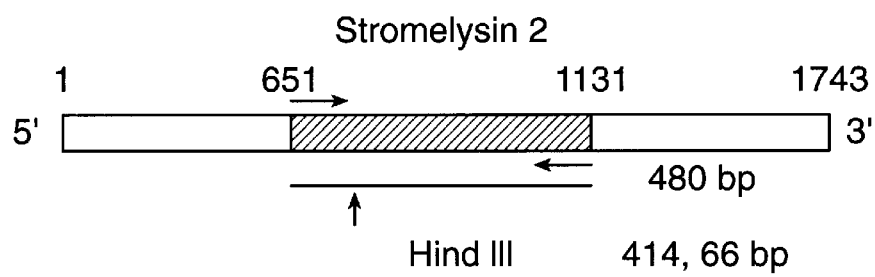
Hind III      414, 66 bp
Stromelysin 3
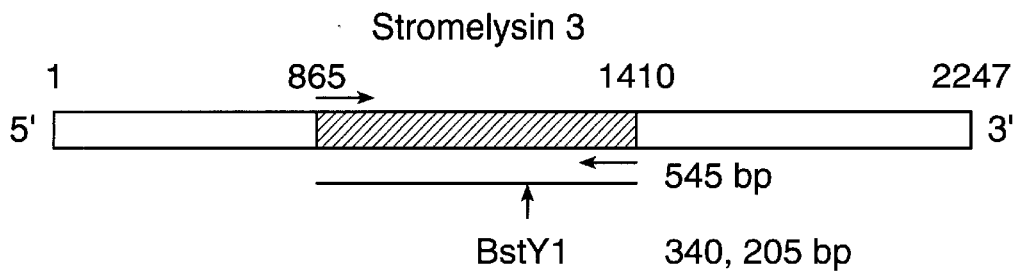
BstY1      340, 205 bp
Matrilysin
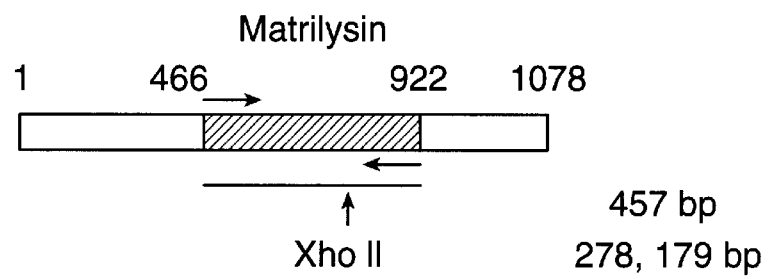
Xho II      278, 179 bp

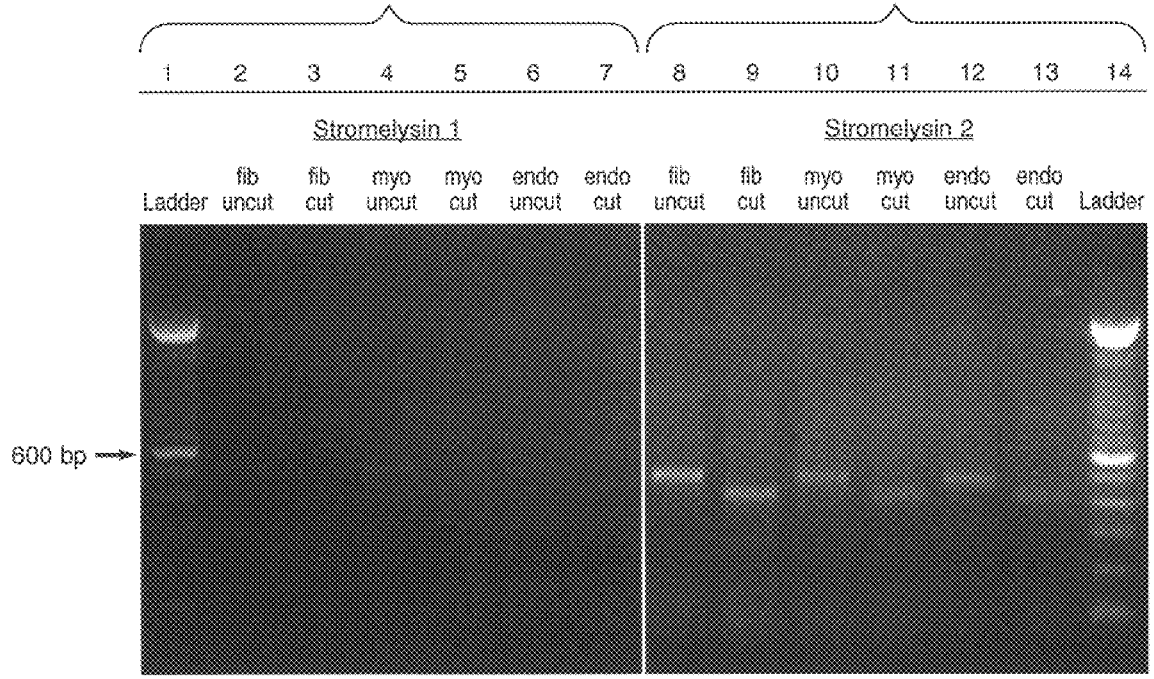

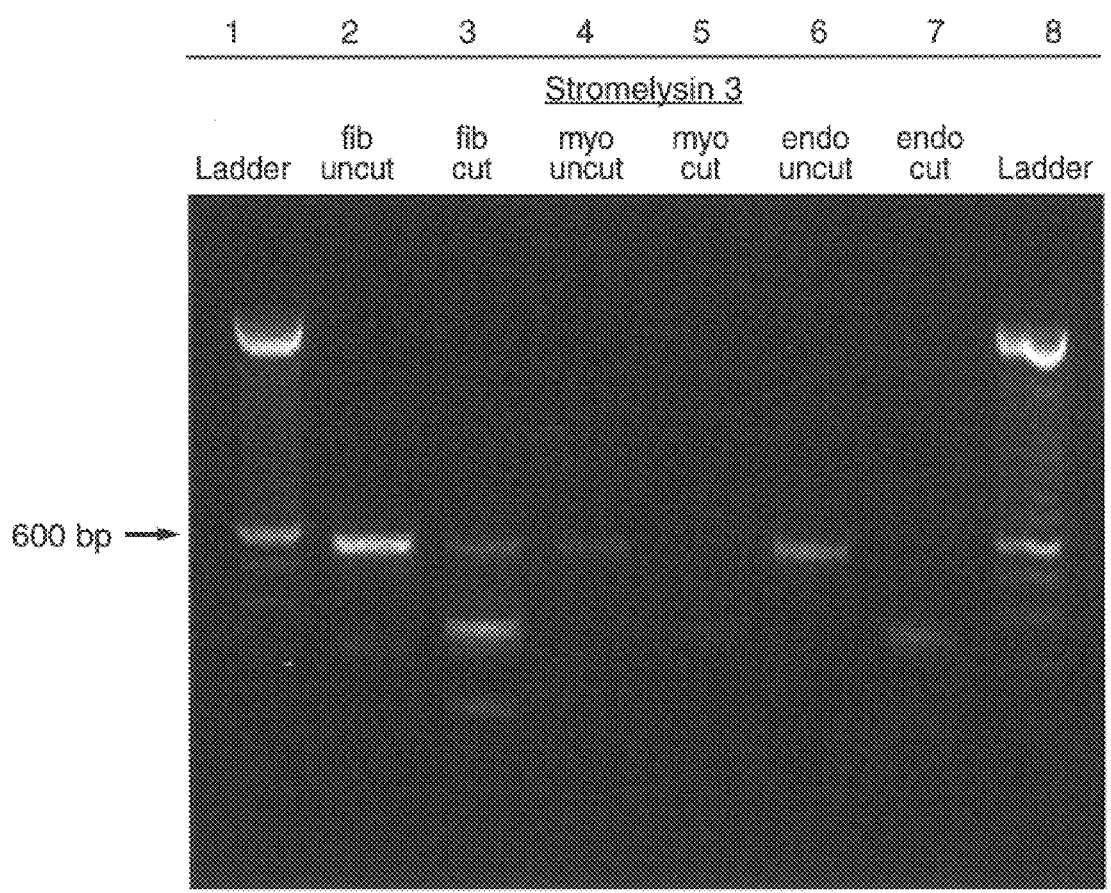

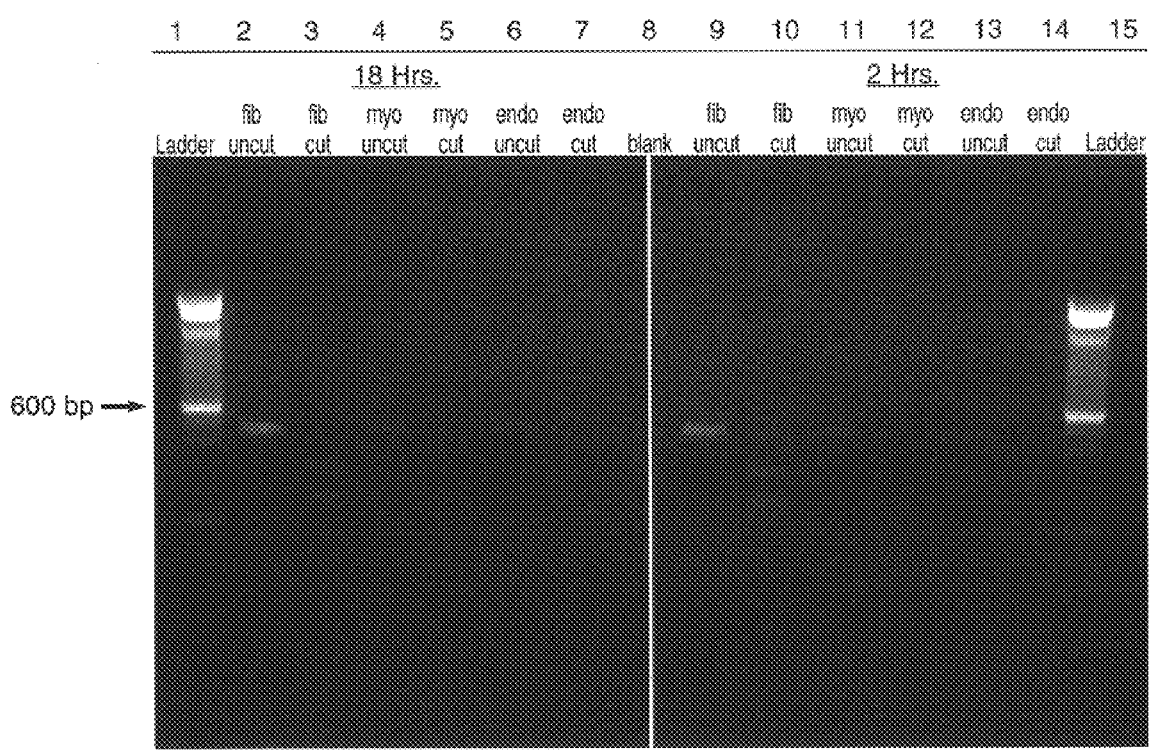

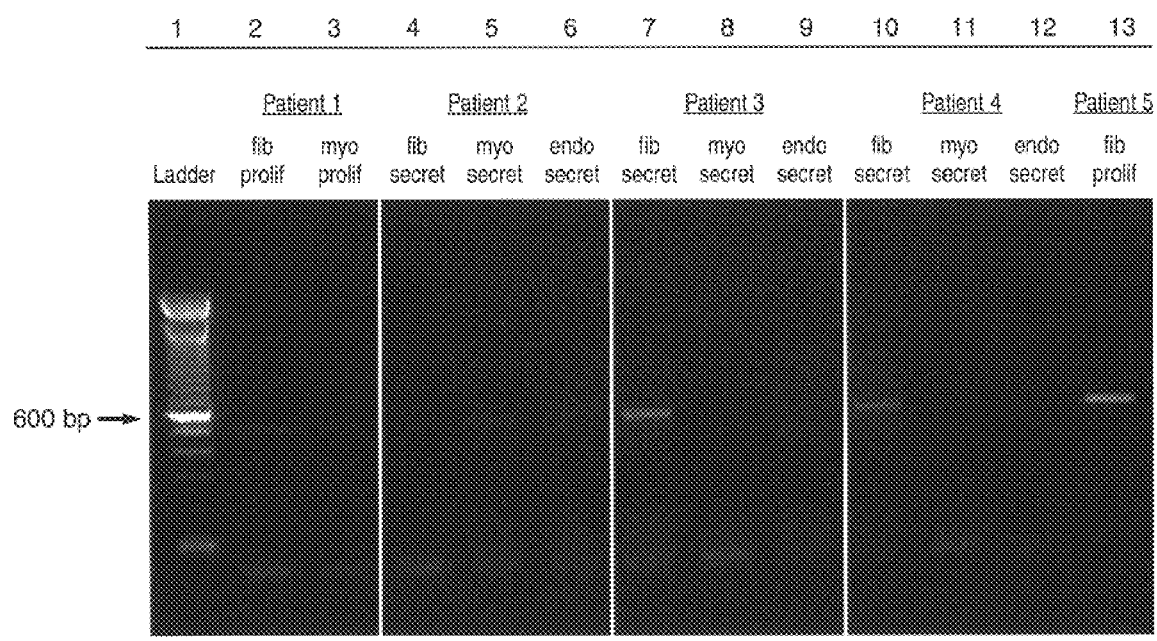

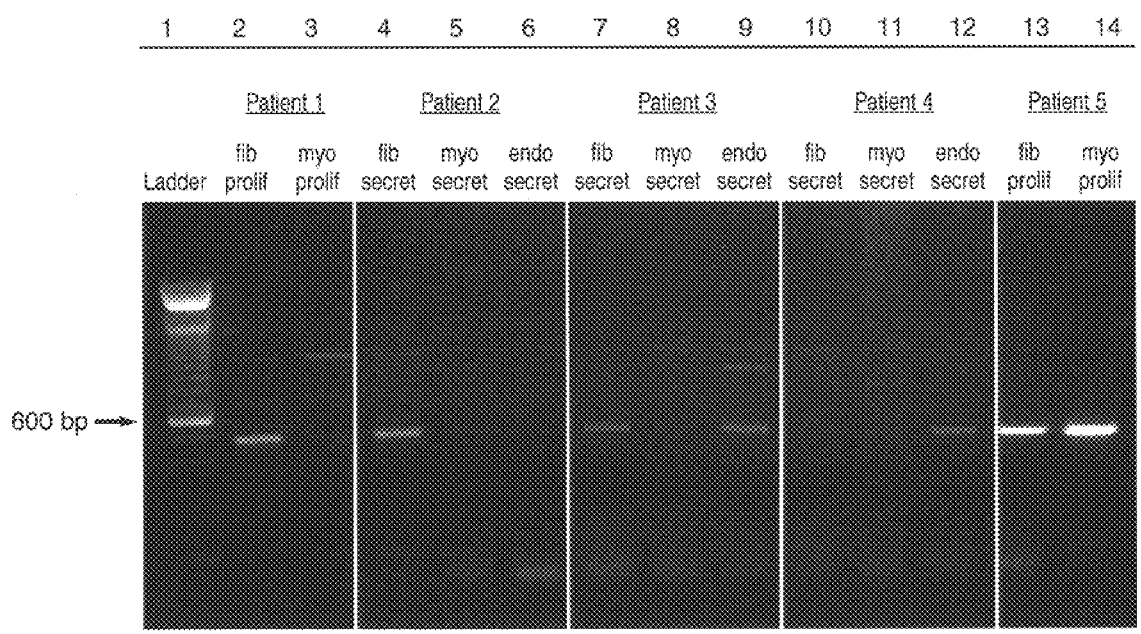

STROMELYSIN 3

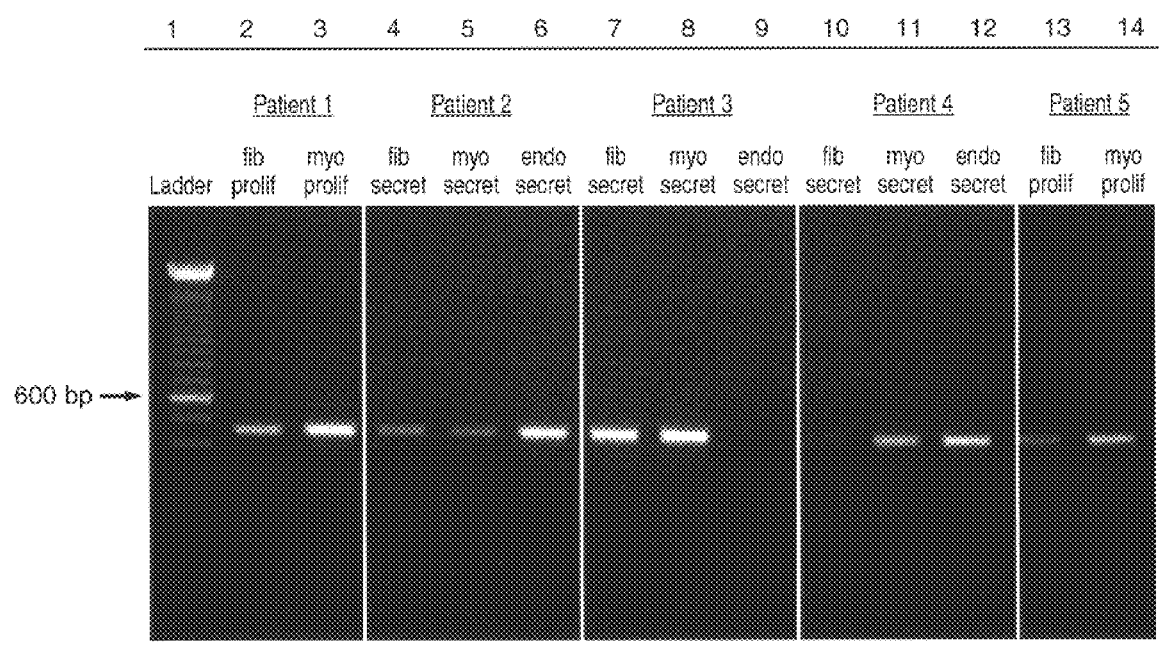

METHODS AND KITS FOR TREATING AND DIAGNOSING LEIOMYOMAS

This application is a continuation of U.S. patent application Ser. No. 09/044,046, filed Mar. 18, 1998, now abandoned, entitled "Methods and Kits for Treating and Diagnosing Leiomyomas" which claims priority from U.S. provisional patent application No. 60/041,261 filed Mar. 18, 1997 also entitled "Methods and Kits for Treating and Diagnosing Leiomyomas".

This invention was made with support under Grant No. HD30496 from the National Institutes of Health. Accordingly, the U.S. government has certain rights in the invention.

BACKGROUND OF THE INVENTION

Throughout this application, various publications are cited by Arabic numerals. The disclosure of these publications is hereby incorporated by reference into this application to describe more fully the state of the art to which this invention pertains.

Uterine leiomyomas (also known as fibroids) are the most common pelvic non-malignant tumors in women, with incidence ranging from 20%–30% in clinical diagnoses of women of reproductive age to 50% in studies conducted at autopsy (1). Uterine fibroids cause abnormal uterine bleeding and pelvic pressure or pain. Presently, hysterectomy is the only cure for leiomyomas, although recent studies have shown that hormonal treatments such as gonadotropin-releasing hormone agonists or the antiprogesterone RU 486 can reduce uterine leiomyoma size by 34%–61% (2–5). Despite the major importance of leiomyomas in clinical gynecology, little is known about their basic biology and the regulation of their growth.

Uterine leiomyomas arise from a single cell, and the resulting tumors grow rapidly and become fibrotic following excess extracellular matrix formation. Analysis of individual fibroids have shown that cells within the tumor exhibit one variant of glucose-6-phosphate dehydrogenase, phosphoglycerokinase, and uniform restriction fragment length polymorphisms of X-chromosomes, verifying that these tumors have a unicellular origin (6–8). Clinical reports have shown that leiomyomas can grow rapidly, particularly during progestin, clomiphene, or tamoxifen therapy (9, 10). The fibrotic nature of the tumor develops as a result of extensive extracellular matrix deposits, which contain greater levels of collagen and proteoglycan than does the myometrium (6, 11). The presence of increased deposits of extracellular matrix in uterine leiomyomas suggests that regulatory mechanisms involved in matrix formation and remodeling may be inappropriately controlled.

Matrix metalloproteinases are enzymes that have been shown to be present in both the epithelial and stromal layers of the normal endometrium during phases of the menstrual cycle when remodeling occurs. The levels of mRNA for several metalloproteinases, including stromelysin-1, stromelysin-2, stromelysin-3 and matrilysin, have been shown to be elevated in the endometrium during the late secretory-menstrual phase and during the early proliferative phase of the cycle (12–14). It is generally accepted that expression of metalloproteinases in the endometrium is coordinated by and dependent upon gonadal steroids.

Similar to the gonadal steroid-dependent growth of the endometrium, myometrial growth is influenced by changes in estrogen and progesterone levels. Removing gonadal steroids by treating patients with GnRH agonists so as to induce a hypoestrogenic state resulted in a reduction of the size of the fibroid and in the entire uterus, while discontinuing GnRH therapy resulted in regrowth of the leiomyoma and the uterus (2, 3). Progesterone has also been shown to promote growth of uterine fibroids (15), and treatment with the antiprogesterone RU 486 has been shown to decrease fibroid size by 49% (5, 16). While the involvement of metalloproteinases in normal or pathologic myometrium is unknown, metalloproteinases are implicated in the steroid-dependent growth of leiomyomas and in the aberrant extracellular matrix formation in leiomyomas compared to myometrium.

Endogenous tissue inhibitors of metalloproteinases (TIMP's) have been shown in many studies to inhibit the catalytic activity of the metalloproteinases. Increases in metalloproteinase expression are often paralleled by low levels of TIMP expression in several diseases including arthritis (17, 18) and invasive cancers (19, 20, 21). The levels of TIMP-1 and TIMP-2 mRNA in the endometrium of women are elevated in the stroma and epithelium of the endometrium during the late secretory and menstrual phases of the menstrual cycle (13, 22). Although metalloproteinases have also been reported to be elevated during these stages of the menstrual cycle, the ratio of TIMP to metalloproteinase may be critical in determining the extent of tissue remodeling in a given tissue. The levels of TIMP-1 and TIMP-2 in leiomyoma and unaffected myometrium are presently unknown.

Therefore, from the art, one of ordinary skill might infer the possibility that metalloproteinases are involved in leiomyoma formation, as evidenced by the steroid-dependent growth of leiomyomas, and further by the lack of normal regulation of extracellular matrix formation in leiomyomas compared to myometrium.

However, despite this possibility and the role of metalloproteinases in endometrial remodeling, one of ordinary skill could not reasonably expect that metalloproteinases in general are involved in leiomyoma formation. Moreover, one of ordinary skill could not reasonably expect that certain metalloproteinases, and not others, are involved in leiomyoma formation.

SUMMARY OF THE INVENTION

This invention provides a method of treating a subject suffering from a leiomyoma which comprises administering to the subject a therapeutically effective dose of an agent which specifically inhibits at least one metalloproteinase selected from the group consisting of stromelysin-2, stromelysin-3 and matrilysin.

This invention also provides a pharmaceutical composition for treating a subject suffering from a leiomyoma which comprises an agent which specifically inhibits at least one metalloproteinase selected from the group consisting of stromelysin-2, stromelysin-3 and matrilysin, and a pharmaceutically acceptable carrier.

This invention further provides a method of treating a subject suffering from a leiomyoma which comprises administering to the subject a therapeutically effective dose of the instant pharmaceutical composition.

This invention further provides a method of treating a subject suffering from a leiomyoma which comprises administering to the subject a therapeutically effective dose of a plurality of agents, each of which specifically inhibits at least one metalloproteinase selected from the group consisting of stromelysin-2, stromelysin-3 and matrilysin.

This invention further provides a pharmaceutical composition for treating a subject suffering from a leiomyoma which comprises a plurality of agents, each of which specifically inhibits at least one metalloproteinase selected from the group consisting of stromelysin-2, stromelysin-3 and matrilysin, and a pharmaceutically acceptable carrier.

This invention further provides a method of treating a subject suffering from a leiomyoma which comprises administering to the subject a therapeutically effective dose of the instant pharmaceutical composition.

This invention further provides a method of determining whether a tumor in a subject is a leiomyoma, which comprises the steps of (a) obtaining a sample of the tumor from the subject; (b) determining the amount of at least one metalloproteinase present in the sample, the metalloproteinase being selected from the group consisting of stromelysin-2, stromelysin-3 and matrilysin; and (c) comparing the amount of each metalloproteinase determined in step (b) to a known standard, thereby determining whether the tumor is a leiomyoma.

This invention further provides a method of determining whether a tumor in a subject is a leiomyoma, which comprises the steps of (a) obtaining a sample of the tumor from the subject; (b) determining the amount of at least one metalloproteinase-encoding mRNA present in the sample, the metalloproteinase being selected from the group consisting of stromelysin-2, stromelysin-3 and matrilysin; and (c) comparing the amount of each metalloproteinase-encoding mRNA determined in step (b) to a known standard, thereby determining whether the tumor is a leiomyoma.

This invention further provides a kit for use in determining whether a tumor in a subject is a leiomyoma, which comprises (a) an agent suitable for determining the amount of a metalloproteinase present in a tumor sample taken from the subject, the metalloproteinase being selected from the group consisting of stromelysin-2, stromelysin-3 and matrilysin; and (b) a known standard with which the amount of each metalloproteinase determined in step (a) can be compared, so as to permit determining whether the tumor is a leiomyoma This invention further provides a kit for use in determining whether a tumor in a subject is a leiomyoma, which comprises (a) an agent suitable for determining the amount of a metalloproteinase-encoding mRNA present in a tumor sample taken from the subject, the metalloproteinase being selected from the group consisting of stromelysin-2, stromelysin-3 and matrilysin; and (b) a known standard with which the amount of each metalloproteinase-encoding mRNA determined in step (a) can be compared, so as to permit determining whether the tumor is a leiomyoma.

Finally, this invention provides a method of determining whether an agent specifically inhibits at least one metalloproteinase selected from the group consisting of stromelysin-2, stromelysin-3 and matrilysin, which comprises determining whether the agent (a) slows the reaction rate of stromelysin-2, stromelysin-3 or matrilysin by a factor of at least 50, and (b) does not slow the reaction rate of any metalloproteinase, other than stromelysin-2, stromelysin-3, matrilysin, and gelatinase a and b, by more than a factor of 25, whereby an agent satisfying the criteria of parts (a) and (b) is one which specifically inhibits at least one metalloproteinase selected from the group consisting of stromelysin-2, stromelysin-3 and matrilysin.

BRIEF DESCRIPTION OF THE FIGURES

These Figures show Northern blots for collagenase, α-tubulin, and stromelysin. In FIG. 1A, samples (5 μg of polyadenylated RNA) from unaffected myometrium (M) and leiomyoma (L) were electrophoresed through 2% formaldehyde-agarose gels and transferred to nitrocellulose. The blots were probed with cDNA's for collagenase (1.5 Kb fragment from pColl-4 (see Materials and Methods, infra)) and re-probed with α-tubulin. The band at 2.9 Kb corresponds to the known size of collagenase mRNA and the band at 1.2 Kb corresponds to the known size of α-tubulin mRNA. In FIG. 1B, the same samples of polyadenylated RNA from FIG. 1A and RNA from two additional patients were probed with cDNA for stromelysin (pStr-33), following the same methods as described above.

FIGS. 2A–2D

These Figures show amplified MMP product detected on 2% agarose gels by ethidium bromide staining as a function of the number of amplification cycles. Stromelysin-1 (FIG. 2A); Stromelysin-2 (FIG. 2B); Stromelysin-3 (FIG. 2C); Lane 1, no cDNA from RT reaction added, stromelysin-3 PCR primers added for 35 cycles; lane 14, "Ladder"=100 bp DNA ladder markers. Matrilysin (FIG. 2D); lane 1, no cDNA from RT reaction added, matrilysin PCR primers added for 38 cycles; lanes 7, 8 and 9, RNA from fibroid, myometrium, and endometrium, respectively, added to the reverse transcriptase step, without random hexamers or MuLV Reverse Transcriptase, followed by matrilysin primers added during PCR for 38 cycles; lane 10, 100 bp ladder molecular weight markers (details for RT-PCR provided in Materials and Methods, infra).

FIGS. 3A–3E

FIG. 3A shows predicted restriction enzyme digestion cut sites (numbers indicate bp of full-length cDNA), and FIGS. 3B–3E show actual restriction digests after electrophoresis of stromelysin-1 (FIG. 3B), stromelysin-2 (FIG. 3C), stromelysin-3 (FIG. 3D), and matrilysin (FIG. 3E), on 2% agarose gels containing ethidium bromide. Ladder=100 bp DNA ladder.

FIGS. 4A–4D

These Figures show a comparison of expression of stromelysin-1 (FIG. 4A), stromelysin-2 (FIG. 4B), stromelysin-3 (FIG. 4C) and matrilysin (FIG. 4D) in patient-matched (i.e. obtained from the same patient), representative samples from uterine fibroids, unaffected myometrium and endometrium collected from each patient. Ladder=100 bp DNA ladder; fib=fibroid; myo=myometrium; endo= endometrium; prolif=proliferative phase of menstrual cycle; secret=secretory phase of menstrual cycle.

FIGS. 5A–5B

Figure 5A:
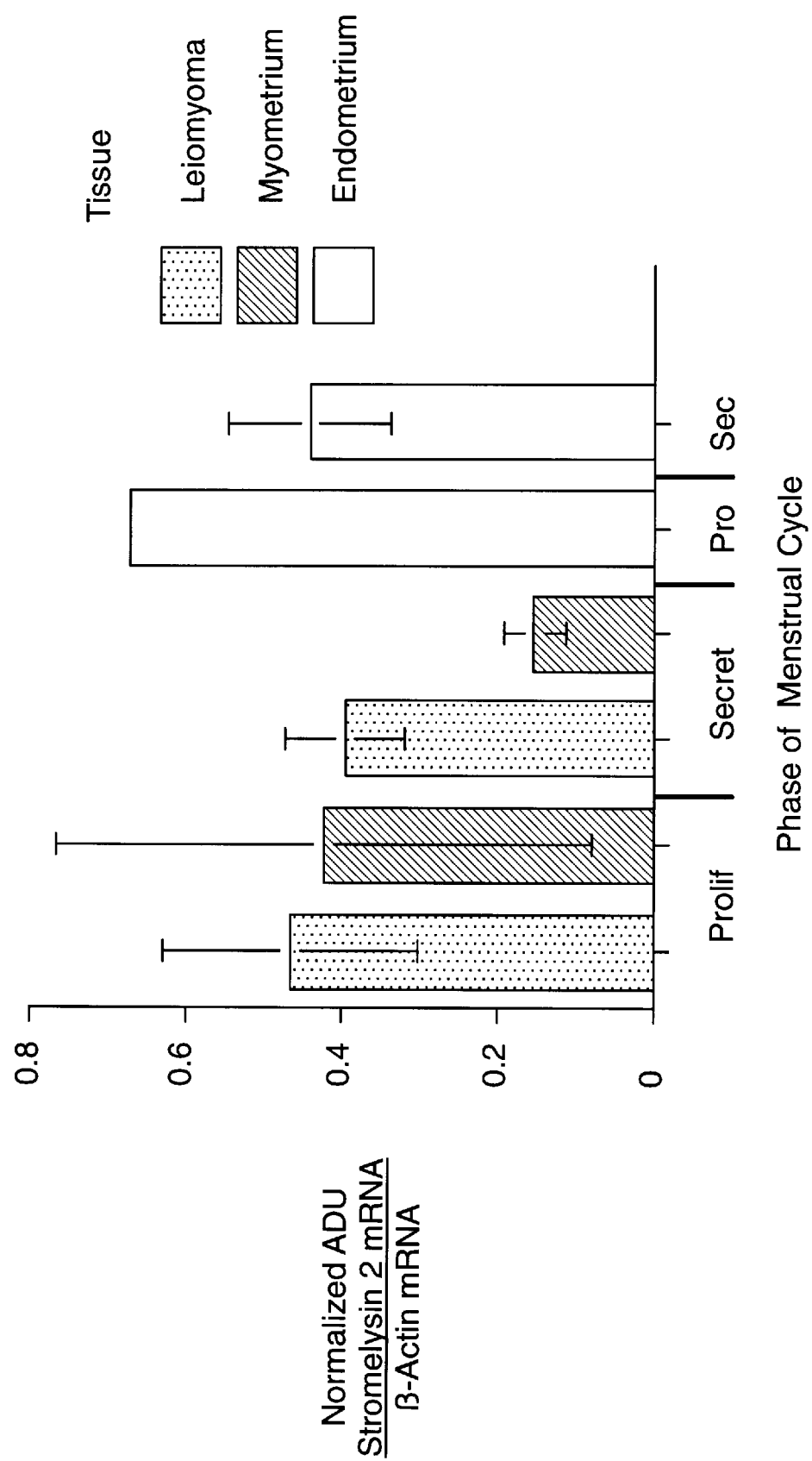
Figure 5B:
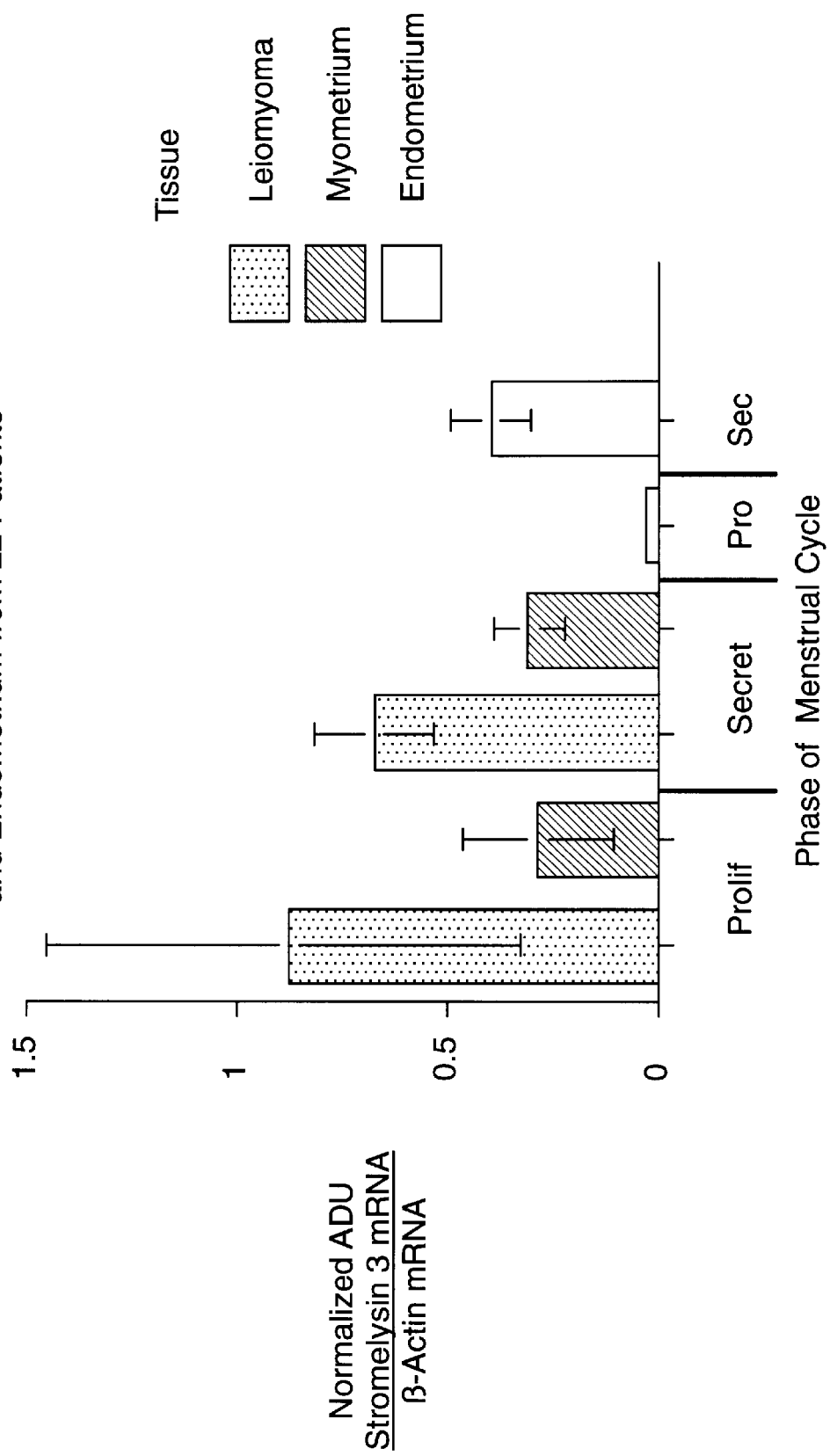

These Figures show a semiquantitative analysis of stromelysin-2 (FIG. 5A) and stromelysin-3 (FIG. 5B) expression from uterine fibroids, myometrium and endometrium in 22 patients. Values shown are the ratio of stromelysin-2 product (FIG. 5A) or stromelysin-3 product (FIG. 5B) relative to β-actin product for each sample, from 2 separate experimental RT-PCR determinations for each patient. Prolif, Pro=proliferative phase of menstrual cycle; Secret, Sec=secretory phase of menstrual cycle. Bars represent means±SEM.

FIG. 6

This Figure shows the expression of tissue inhibitor of metalloproteinase-2 (TIMP-2) in patient matched, representative samples from uterine fibroids, myometrium and endometrium. Ladder=100 bp DNA ladder; fib=fibroid; myo=myometrium; endo=endometrium; prolif=proliferative phase of menstrual cycle; secret=secretory phase of menstrual cycle; atroph=atrophic uterus.

FIG. 7

This Figure shows a comparison of EGF mRNA. expression in uterine leiomyoma, myometrium and endometrium. Levels of TIMP-2 product from 2 separate experimental RT-PCR determinations for each patient were normalized to the level of β-actin product determined from each of the same 2 experiments. Values shown are the ratio of TIMP-2 product after 30 cycles of amplification to β-actin product after 28 cycles of amplification for each sample. Pro= proliferative phase of menstrual cycle; Sec=secretory phase of menstrual cycle. Bars represent means±SEM.

DETAILED DESCRIPTION OF THE INVENTION

This invention provides a method of treating a subject suffering from a leiomyoma which comprises administering to the subject a therapeutically effective dose of an agent which specifically inhibits at least one metalloproteinase selected from the group consisting of stromelysin-2, stromelysin-3 and matrilysin.

As used herein, "subject" means any animal, such as a mouse, susceptible to leiomyomas. Other animals include, by way of example, rats, dogs, guinea pigs, ferrets, rabbits, and primates. In the preferred embodiment, the subject is a human. Additionally, "leiomyoma" includes both stomach and uterine leiomyomas. In the preferred embodiment, the leiomyoma is a uterine leiomyoma.

In one embodiment, the agent used in the instant method is a small organic molecule. Examples of small organic molecules which may be used include imidazole hydroxyamates, such as

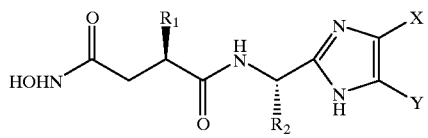

wherein $R_2$, X and Y are $CH_2CHMe_2$, H and Ph, respectively, and $R_1$ is $CH_2CHMe_2$ or $C-C_6H_{11}$.

In another embodiment, the agent is a polypeptide. Examples of polypeptides which may be used in the instant invention include, but are not limited to, a polypeptide which comprises at least a portion of a matrix metalloproteinase inhibitor.

As used herein, an agent "specifically inhibits" stromelysin-2, stromelysin-3 or matrilysin if it slows the enzyme's reaction rate by a factor of at least 50 ("first factor"), and does not slow the reaction rate of any other metalloproteinase, except for stromelysin-2, stromelysin-3, matrilysin, and gelatinase a and b, by more than a factor of 25 ("second factor"). In another embodiment, the first and second factors are 500 and 5, respectively. In the preferred embodiment, the first and second factors are 1000 and 1, respectively. Methods of measuring enzyme reaction rates and enzyme inhibition are standard in the art.

In one embodiment, the agent specifically inhibits only one metalloproteinase selected from stromelysin-2, stromelysin-3 or matrilysin. In another embodiment, the agent specifically inhibits two metalloproteinases selected from the group consisting of stromelysin-2, stromelysin-3 and matrilysin. In a further embodiment, the agent specifically inhibits each of stromelysin-2, stromelysin-3 and matrilysin.

This invention also provides a method of treating a subject suffering from a leiomyoma which comprises administering to the subject a therapeutically effective dose of a plurality of agents, each of which specifically inhibits at least one metalloproteinase selected from the group consisting of stromelysin-2, stromelysin-3 and matrilysin.

This invention further provides a pharmaceutical composition for treating a subject suffering from a leiomyoma which comprises an agent which specifically inhibits at least one metalloproteinase selected from the group consisting of stromelysin-2, stromelysin-3 and matrilysin, and a pharmaceutically acceptable carrier.

This invention also provides a pharmaceutical composition for treating a subject suffering from a leiomyoma which comprises a plurality of agents, each of which specifically inhibits at least one metalloproteinase selected from the group consisting of stromelysin-2, stromelysin-3 and matrilysin, and a pharmaceutically acceptable carrier.

Pharmaceutically acceptable carriers are well known to those skilled in the art and include, but are not limited to, 0.01–0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

This invention further provides a method of treating a subject suffering from a leiomyoma which comprises administering to the subject a therapeutically effective dose of one of the instant pharmaceutical compositions.

As used herein, administering may be effected or performed using any of the various methods known to those skilled in the art. The administering may comprise, for example, administering intravenously, intramuscularly, and subcutaneously.

A therapeutically effective dose of an instant pharmaceutical composition is a dose sufficient to reduce by 50% either the leiomyoma size or the severity of a related symptom (e.g., uterine bleeding and uterine inflammation) in an afflicted subject. In the preferred embodiment, the treatment of an afflicted subject will comprise administering a plurality of therapeutically effective doses over a period of time. The doses and time periods can be determined through known methods. In one embodiment, the therapeutically effective dose is from 30 ug/kg to 30 mg/kg for polypeptide agents and from 60 ug/kg to 30 mg/kg for small organic agents. In the another embodiment, the therapeutically effective dose is from 300 ug/kg to 3 mg/kg for polypeptide agents and from 600 ug/kg to 3 mg/kg for small organic agents.

The various embodiments of the term "subject", the leiomyoma type, and nature and behavior of agents recited supra for the instant methods using the agent(s) alone apply to the instant pharmaceutical compositions and methods using same.

This invention further provides two diagnostic methods of determining whether a tumor in a subject is a leiomyoma. The first method comprises the steps of (a) obtaining a sample of the tumor from the subject; (b) determining the amount of at least one metalloproteinase present in the sample, the metalloproteinase being selected from the group consisting of stromelysin-2, stromelysin-3 and matrilysin; and (c) comparing the amount of each metalloproteinase determined in step (b) to a known standard, thereby determining whether the tumor is a leiomyoma.

The second method comprises the steps of (a) obtaining a sample of the tumor from the subject; (b) determining the amount of at least one metalloproteinase-encoding mRNA present in the sample, the metalloproteinase being selected from the group consisting of stromelysin-2, stromelysin-3 and matrilysin; and (c) comparing the amount of each metalloproteinase-encoding mRNA determined in step (b) to a known standard, thereby determining whether the tumor is a leiomyoma.

Methods of obtaining tumor samples from inflicted subjects, including samples enriched for protein and mRNA, are routine in the art and are exemplified in the Experimental Details section infra. Methods of determining amounts of a given protein in a sample are well known and include, but are not limited to, immunohistochemistry, immunoblotting, enzyme activity assays, and zymography. Methods of determining amounts of mRNA in a sample are well known and include, but are not limited to, Northern blotting, RT-PCR, in situ detection, and combinations thereof.

In the instant methods, the "known standards" may comprise amounts of metalloproteinase or corresponding mRNA (whichever is applicable) known to be present in leiomyoma, normal myometrium, or both. In the preferred embodiment, the "known standards" comprise amounts of metalloproteinase or corresponding mRNA (whichever is applicable) known to be present in both leiomyoma and in normal myometrium.

Also, in one embodiment of the instant diagnostic methods, the metalloproteinase is stromelysin-3. In the preferred embodiment, the metalloproteinase is stromelysin-2, stromelysin-3 and matrilysin.

This invention further provides two kits for use in determining whether a tumor in a subject is a leiomyoma. The first kit comprises (a) an agent suitable for determining the amount of a metalloproteinase present in a tumor sample taken from the subject, the metalloproteinase being selected from the group consisting of stromelysin-2, stromelysin-3 and matrilysin; and (b) a known standard with which the amount of each metalloproteinase determined in step (a) can be compared, so as to permit determining whether the tumor is a leiomyoma.

In one embodiment, the agent suitable for determining the amount of a metalloproteinase is an antibody. The antibody may be labeled (using a detectable marker) or unlabeled (when used in conjunction with a labeled antibody); whole polyclonal, whole monoclonal, or a fragment thereof; and naturally occurring or non-naturally occurring. The detectable marker may be, for example, radioactive or fluorescent. Methods of making and using such antibodies are well known in the art.

The second kit comprises (a) an agent suitable for determining the amount of a metalloproteinase-encoding mRNA present in a tumor sample taken from the subject, the metalloproteinase being selected from the group consisting of stromelysin-2, stromelysin-3 and matrilysin; and (b) a known standard with which the amount of each metalloproteinase-encoding mRNA determined in step (a) can be compared, so as to permit determining whether the tumor is a leiomyoma.

In one embodiment, the agent suitable for determining the amount of a metalloproteinase-encoding mRNA is a detectable nucleic acid probe. Such probes and methods of making same are known in the art, and are exemplified in the Experimental Details section infra.

Finally, this invention provides a method of determining whether an agent specifically inhibits at least one metalloproteinase selected from the group consisting of stromelysin-2, stromelysin-3 and matrilysin, which comprises determining whether the agent (a) slows the reaction rate of stromelysin-2, stromelysin-3 or matrilysin by a factor of at least 50, and (b) does not slow the reaction rate of any metalloproteinase, other than stromelysin-2, stromelysin-3, matrilysin, and gelatinase a and b, by more than a factor of 25, whereby an agent satisfying the criteria of parts (a) and (b) is one which specifically inhibits at least one metalloproteinase selected from the group consisting of stromelysin-2, stromelysin-3 and matrilysin.

Methods of quantitatively determining the extent to which an agent slows the reaction rate of a metalloproteinase are known in the art. Such methods include, but are not limited to, fluorometric assays (80). Metalloproteinases other than stromelysin-2, stromelysin-3, matrilysin, and -gelatinase a and b include, by way of example, human fibroblast collagenase (also known in the art as MMP-1).

This invention will be better understood by reference to the Experimental Details which follow, but those skilled in the art will readily appreciate that the specific experiments detailed are only illustrative of the invention as described more fully in the subject inventions which follow thereafter.

Experimental Details

The following experiments have been conducted to determine the level of mRNA expression of certain members of the matrix metalloproteinase family in uterine leiomyomas as compared to unaffected myometrium and to endometrium. The expression of collagenase and stromelysin 1 mRNA were measured by Northern blotting and levels of stromelysin-1, stromelysin-2, stromelysin-3, and matrilysin mRNA were measured by semiquantitative reverse transcriptase polymerase chain reaction (RT-PCR). The levels of endogenous tissue inhibitors of metalloproteinases-1 and -2 (TIMP-1 and TIMP-2) mRNA were determined using RT-PCR.

Materials and Methods

Patients

Tissue specimens were obtained from premenopausal women with symptomatic uterine fibroids who were not receiving any type of hormonal or drug therapy and were undergoing elective hysterectomies. Collection of tissues was obtained under a consent for use of discarded human tissue in accordance with the Brigham & Women's Hospital policy. The stage of the menstrual cycle was determined by histological dating of the endometrium for both proliferative and secretory phase samples.

Collection of Tissue and Preparation of RNA

Leiomyoma tissue samples were cut from near the center of the tumor to avoid potential myometrial contamination. Myometrial tissues were cut well away from the endometrial layer and from the leiomyoma. Endometrial tissue was scraped from the uterine surface with a scalpel blade, thus removing the functionalis layer but leaving the lower basalis intact so as to avoid possible contamination with underlying myometrium. Tissues were obtained within 30 minutes of removal from the patient and were homogenized in 4 M guanidine isothiocyanate for preparing total RNA (23).

Northern Blotting

Northern blots were performed following previously established methods (24). Briefly, polyadenylated mRNA was purified from total RNA and 5 $\mu$g of the polyA RNA were electrophoresed, transferred to nitrocellulose (Schleicher and Schuell, Keene, N.H.) and probed for collagenase, stromelysin-1 and α-tubulin mRNA. Following hybridization and washing (methods described supra), the blots were exposed to autoradiographic film for 24 hours and then the films were developed. The cDNA's for collagenase and stromelysin-1, used for probing the northern blots, were prepared according to known methods (17).

RT-PCR

Equal amounts of RNA (1 μg) from leiomyoma, myometrium and endometrium samples were added to tubes for first strand synthesis, following the manufacturers' recommended conditions for reverse transcription (Perkin Elmer Cetus; GeneAmp RNA PCR). Aliquots (3–9 μl) of the reverse transcribed products were removed and added to fresh tubes for PCR amplification of the target DNA. Briefly, the PCR amplification mixture contained a final concentration of 2 mM $MgCl_2$, 200 μM dNTPs, 0.2 μM primers and 2.5 U Taq Polymerase in a 100 μl reaction tube (Perkin Elmer Cetus). Table 1 provides specific amounts of RT product, sequences of the oligos and numbers of cycles of amplification for each amplified product.

TABLE 1

Conditions for RT-PCR Amplification

| MMP product | Amount of cDNA | Temp (° C.)/ # of cycles | Oligo sequence |
|---|---|---|---|
| Stromelysin-1 | 6 μl | 56° C./38 | 5'-1 and 3'-A |
| Stromelysin-2 | 3 μl | 56° C./35 | 5'-2 and 3'-B |
| Stromelysin-3 | 3 μl | 56° C./30 | 5'-3 and 3'-C |
| Matrilysin | 6 μl | 56° C./38 | 5'-4 and 3'-D |
| β-Actin | 3 μl | 56° C./28 | 5'-5 and 3'-E* |
| Transferrin Receptor | 6 μl | 56° C./35 | 5'-6 and 3'-F* |
| TIMP-1 | 3 μl | 56° C./30 | 5'-7 and 3'-G§ |
| TIMP-2 | 3 μl | 56° C./30 | 5'-8 and 3'-H§ |

| | | |
|---|---|---|
| 5'-1 | AATTTATTTCTCGTTGCTGCTCA | 3'-A |
| | GGGTGTGGATGCCTCTTGGGTAT | |
| 5'-2 | CATTCCTTGTGCTGTTGTGTCTG | 3'-B |
| | CTGCTTGTACCTCATTTCCTCTG | |
| 5'-3 | GAGCCAGACGCCCCGCCAGATGC | 3'-C |
| | TTCCAGAGCCTTCACCTTCACAG | |
| 5'-4 | GTTGTATGKGGMACTGCTGACATCA | 3'-D |
| | TGGAGTGGAGGAACAGTGCTTATCA | |
| 5'-5 | ATCTGGCACCACACCTTCTACAATG- | 3'-E |
| | CGTCATACTCCTGCTTGCTGATCCA- | |
| | AGCTGCGCATCTGC | |
| 5'-6 | CCACCATCTCGGTCATCAGGATTGCCT | 3'-F |
| | TTCTCATGGAAGCTATGGGTATCACAT | |

*Human β-actin and transferrin receptor amplimer sets from Clontech Labs., Inc.
§ Human TIMP-1 and TIMP-2 amplimers from Nuovo et al., 1995 (25).

Oligonucleotides were either synthesized (Cruachem, Sterling, Va.) or purchased (Clontech Labs., Inc., Palo Alto, Calif.). The amplification protocol consisted of denaturation at 95° C. for 1 minute, annealing at 55–60° C. for 1 minute (see Table 1), and extension at 72° C. for 2 minutes, with a final cycle including extension at 72° C. for 5 minutes. The completed reaction was maintained at 4° C. overnight. Reverse transcription and PCR were performed using a GeneAMP 9600 Thermal Cycler (Perkin Elmer, Norwalk, Conn.). The number of cycles for amplification of each gene product was chosen from cycle numbers that yielded linear increases in product. The PCR products were separated in 2% agarose gels (BioRad, Hercules, Calif.) containing 0.2 μg/ml ethidium bromide (Sigma, St. Louis, Mo.). The intensity of the amplified product bands were recorded on Polaroid film, and quantitated on a Hewlett Packard scanner.

In experiments where semiquantitative analysis of gene expression was measured by RT-PCR, two endogenous genes, transferrin receptor and actin (Clontech Labs, Inc., Palo Alto, Calif.), were either amplified in the same tube as a co-amplified product, or in parallel reaction tubes, respectively. Transferrin receptor was chosen as an endogenous gene to co-amplify in the same tube because its level of expression and amplification is similar to low-abundance gene products (manufacturer's recommendations, Clontech Labs, Inc.). Actin, which is normally expressed at a higher level compared to low-abundance mRNA was not well suited for co-amplification in the same tube, but has been used previously as an endogenous control for gene amplification. Therefore, actin was amplified in parallel tubes to provide a second estimator of input RNA for normalization of RT-PCR results. Expression of the various metalloproteinases was normalized to actin and the relative level of expression verified by comparison to levels of transferrin receptor. The normalized results, based on actin mRNA levels, were then compared to provide an average normalized level of expression in samples from leiomyoma, myometrium and endometrium. The amount of amplified product obtained with the matrilysin oligo primers in the presence or absence of transferrin receptor oligo primers varied, suggesting that the matrilysin primers and transferrin receptor primers were not compatible for co-amplification. Therefore, only actin mRNA levels were used to normalize expression of matrilysin mRNA.

To confirm the identity of the amplified product, amplified products of fibroid, myometrium and endometrium were pooled separately and subjected to restriction digestion. The amplified products were purified from RT-PCR reactions on QIAgen columns (QIAgen, Chatsworth, Calif.) and aliquots of the purified PCR product were added to restriction digestion reactions. The sequence of the PCR product was determined in additional aliquots of the same purified PCR products by the Brigham and Women's Core Sequencing Facility using ABS 2600 equipment.

Statistics

The normalized levels of matrix metalloproteinases in leiomyoma, myometrium and endometrium were compared in a 2-factor analysis of covariance. The two factors were the phase of the menstrual cycle, either proliferative or secretory, and the source of the tissue, either leiomyoma, myometrium or endometrium, and the covariate was the patient. Differences in expression between tissues and phases of the menstrual cycle were determined using Fisher's Protected Least Significant Difference test in the SuperAnova statistics package (Abacus Concepts, Inc., Berkeley, Calif.).

Results

Figure 1A:
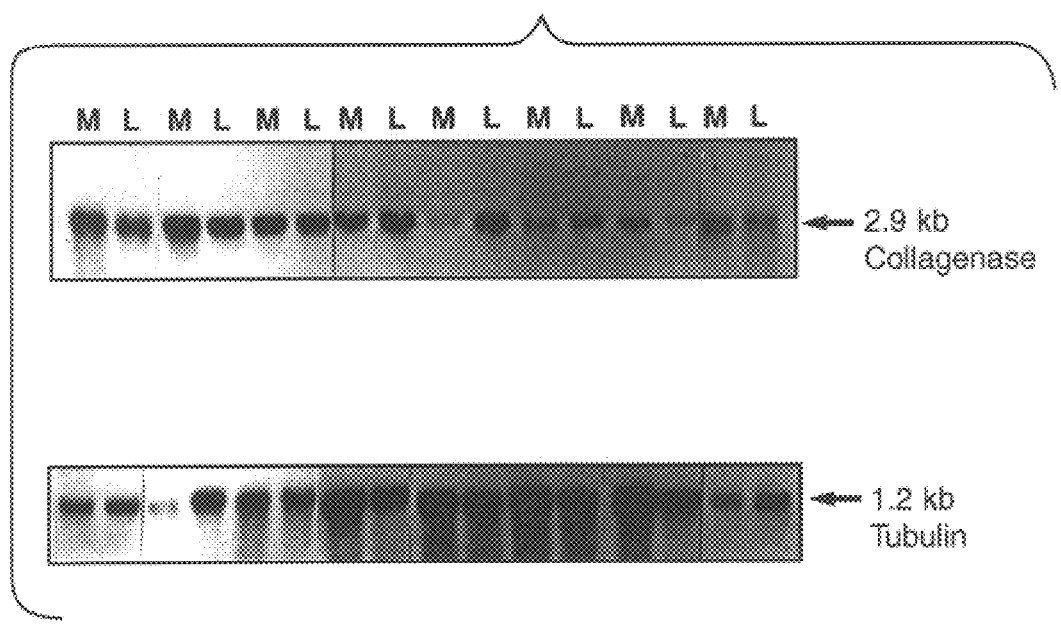
FIGS. 1A and 1B
Figure 1B:
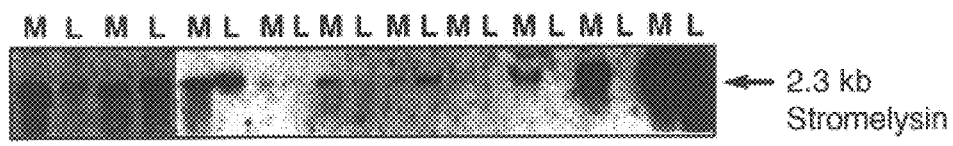

Expression of collagenase and stromelysin-1 mRNA was compared between matched samples of polyA RNA prepared from leiomyoma and myometrium from 8 or 10 patients, respectively (FIGS. 1A and 1B). To verify equal sample loading of polyA RNA, levels of α-tubulin mRNA were compared. Levels of collagenase mRNA were similar in leiomyoma and myometrium from individual patients, with few exceptions. Levels of stromelysin-1 mRNA in leiomyoma compared to myometrium varied among patients, and in several patients, levels of stromelysin mRNA in leiomyoma were too low for detection by Northern blotting. Results from Northern blots of polyA mRNA failed to demonstrate a consistent difference in expression of either collagenase or stromelysin-1 mRNA between leiomyoma and myometrium.

To determine if the levels of other MMP mRNAs were expressed differently in leiomyoma compared to myometrium, a survey of MMP mRNA expression was performed using RT-PCR methods. The oligonucleotide primers and the conditions for the amplification of stromelysin-1, stromelysin-2, stromelysin-3, and matrilysin are listed in Table 1. The oligonucleotides chosen were found to provide optimal annealing conditions as determined in OLIGO (version 4.0) (National Biosciences, Inc., Plymouth, Minn.), and the specificity of the oligonucleotides for the predicted product was confirmed by comparison to known sequences in GenBank using the FASTA comparison (Genetics Computer Group, Madison, Wis.) The predicted sizes of RT-PCR products were: stromelysin-1, 505 bp; stromelysin-2, 480 bp; stromelysin-3, 545 bp; and matrilysin, 457 bp. FIGS. 2A through 2D show the amount of amplified product detected in samples containing elevated levels of product on 2% agarose gels by ethidium bromide staining as a function of the number of amplification cycles. The number of amplification cycles for the various metalloproteinases was chosen based on the results from these experiments (see Table 1). The cycle numbers that were used in subsequent studies were within the linear portion of the amplification cycle curve. The oligonucleotide primers for TIMP-1 and TIMP-2 have been characterized previously (25) and were validated for linear increase in product for these experiments (data not shown). TIMP-1 was amplified for 30 cycles and TIMP-2 was amplified for 34 cycles.

To insure that the detected amplified products shown in FIGS. 2A–2D corresponded to the correct mRNA, restriction digestion analyses of the amplified products were performed. FIG. 3A shows a diagrammatic representation of the predicted digestion pattern of the amplified products, cut with the appropriate restriction enzymes. FIGS. 3B–3E display the actual restriction enzyme digestion analysis of the various products in the presence (cut) or absence (uncut) of restriction enzyme from fibroid, myometrium, and endometrium RNA samples following RT-PCR amplification and product purification. The amplified stromelysin-1 product was predicted to be 505 bp and the amplified product was cut twice by Hind III, producing 3 fragments, i.e., a faint band that corresponds to the 264 bp fragment (FIG. 3B) and 2 smaller fragments of 68 and 173 bp that were not visible with ethidium bromide staining. The amplified stromelysin-2 was predicted to be 480 bp (FIG. 2A) and the amplified product was cut once by Hind III into 2 fragments, producing a visible band at 414 bp and a smaller fragment (66 bp) not visible on the gels (FIG. 3C). The amplified stromelysin-3 was predicted to be 545 bp and the amplified product was cut by BstY1 into two fragments of 340 bp and 205 bp that were both visible (FIG. 3D). The amplified matrilysin product was predicted to be 447 bp, and the amplified product was cut by XhoII into two fragments of 278 bp and 169 bp that were both visible (FIG. 3E). The restriction enzyme digestion patterns for the RT-PCR products of all 4 metalloproteinases examined were consistent with their predicted digestion pattern, providing evidence that the amplified products correspond to the desired metalloproteinase mRNA.

Figure 4C:
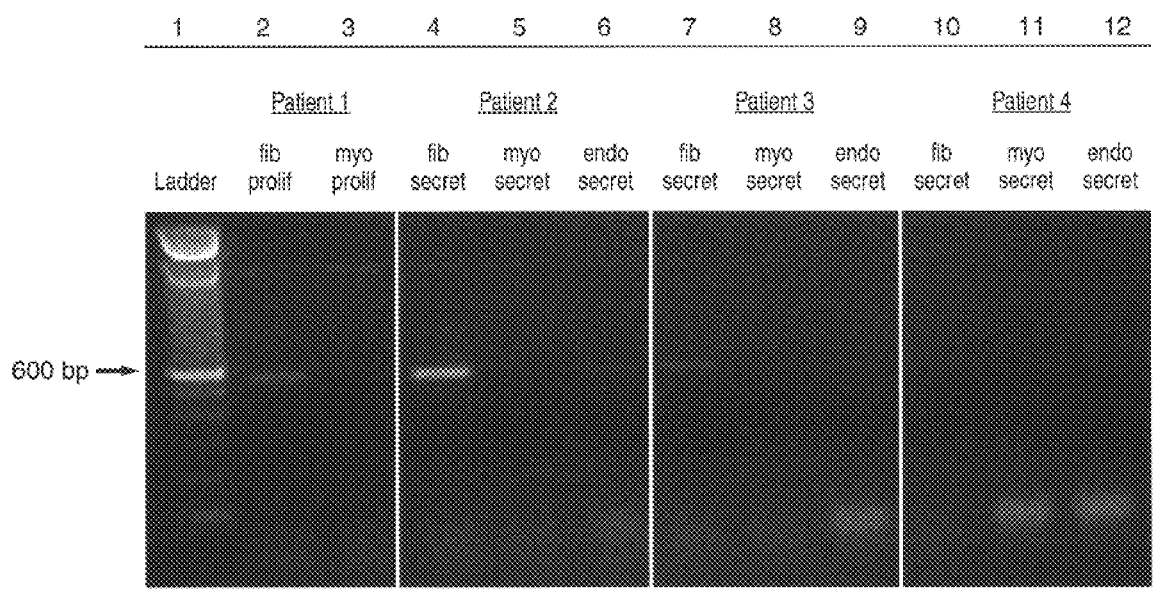

The levels of stromelysin-1, stromelysin-2, stromelysin-3, matrilysin, TIMP-1 and TIMP-2 mRNA were measured by semiquantitative RT-PCR, normalized to actin, and the relative level of expression of each enzyme mRNA was compared between leiomyoma and myometrium, and between myometrium and endometrium (FIGS. 4A–4D). Levels of stromelysin-1 mRNA were low in all 3 uterine tissues examined. Within given patients there was a tendency for stromelysin-1 mRNA to be elevated in fibroids compared to myometrium (compare patients 1, 3 and 4 with patient 2 in FIG. 3A) However, levels of stromelysin-1 mRNA were not consistently greater in fibroids than in myometrium. The low level of expression and the variable expression of stromelysin-1 mRNA in leiomyoma compared to myometrium determined by RT-PCR were in agreement with earlier Northern blotting results (FIG. 1). Stromelysin-2 and stromelysin-3 mRNA were amplified in the presence of their respective oligonucleotides and in addition, transferrin receptor mRNA was co-amplified as an endogenous control to confirm equal loading of RNA for RT-PCR. The transferrin receptor amplimers (Clontech, Palo Alto, Calif.) amplified a region of approximately 1300 bp of the human transferrin receptor cDNA. Levels of stromelysin-2 (FIG. 4B) and stromelysin-3 (FIG. 4C) mRNA were greater in leiomyoma compared to myometrium, particularly during the secretory phase of the menstrual cycle. Similar results (not shown) were obtained when either stromelysin-2 or stromelysin-3 mRNA were amplified and the results normalized to human $\beta$-actin mRNA amplified in parallel reaction tubes. Levels of stromelysin-2 and stromelysin-3 mRNA in the endometrium were not significantly different between phases of the menstrual cycle. However, only 2 of the 6 patients in the proliferative phase group had sufficient endometrium to obtain a biopsy specimen for analysis. Matrilysin mRNA was expressed in all three tissues examined, and the level of matrilysin mRNA was not different between leiomyoma and myometrium during either phase of the cycle (FIG. 4D). Levels of matrilysin mRNA in the endometrium appeared to be greater during the proliferative phase compared to the secretory phase. These results suggest that stromelysin-2 and stromelysin-3 are involved in the greater level of extracellular matrix deposition that occurs in leiomyoma relative to myometrium.

The levels of stromelysin-2 and stromelysin-3 mRNA in leiomyoma compared to myometrium appeared to be elevated in a consistent manner in the 22 patients examined (representative samples shown in FIGS. 4B and 4C). Quantitative determinations of the levels of stromelysin-2 and stromelysin-3 mRNA, normalized relative to actin mRNA, were compared between leiomyoma and unaffected myometrium for the 22 patients and the levels of metalloproteinases were analyzed by analysis of covariance. Among the 22 patients, the levels of stromelysin-2 and stromelysin-3 were significantly greater in leiomyoma compared to unaffected myometrium, regardless of the phase of menstrual cycle ($P<0.025$). When the levels of stromelysin-2 and stromelysin-3 mRNA were compared as a function of the menstrual cycle, stromelysin-2 mRNA (FIG. 5A; $P<0.04$) and stromelysin-3 mRNA (FIG. 5B; $P<0.04$) were significantly greater in leiomyoma compared to myometrium during the secretory phase, but not during the proliferative phase. An accurate estimate of the levels of stromelysin-2 or stromelysin-3 in the proliferative phase of the cycle may have been more difficult due to the smaller number of patients sampled in the proliferative phase (n=6) relative to the secretory phase (n=16).

Figure 6:
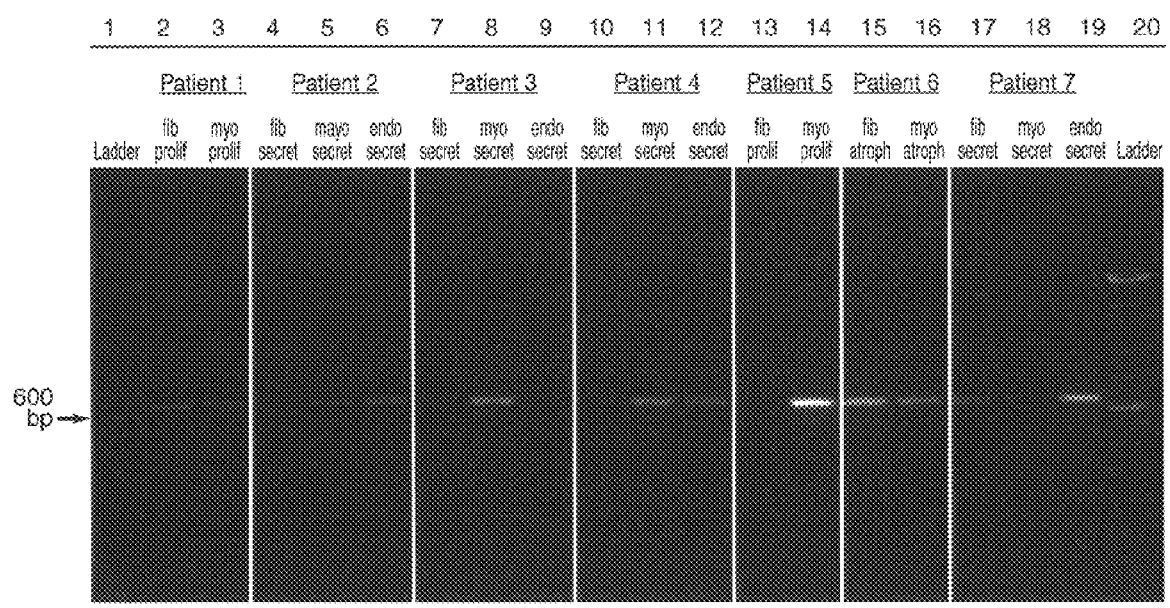

The levels of TIMP-1 and TIMP-2 mRNA were measured to determine if the increased levels of stromelysin-2 and stromelysin-3 mRNA in leiomyoma were accompanied by compensatory changes in levels of TIMP expression. The levels of TIMP-1 were equivalent among leiomyoma, myometrium and endometrium and varied little between proliferative and secretory phases (data not shown). Levels of TIMP-2 tended to be lower in leiomyoma compared to myometrium during the proliferative phase of the cycle (FIG. 6; n=6, P=0.15), and levels of TIMP-2 mRNA were similar in leiomyoma and myometrium during the secretory phase of the cycle.

Figure 7:
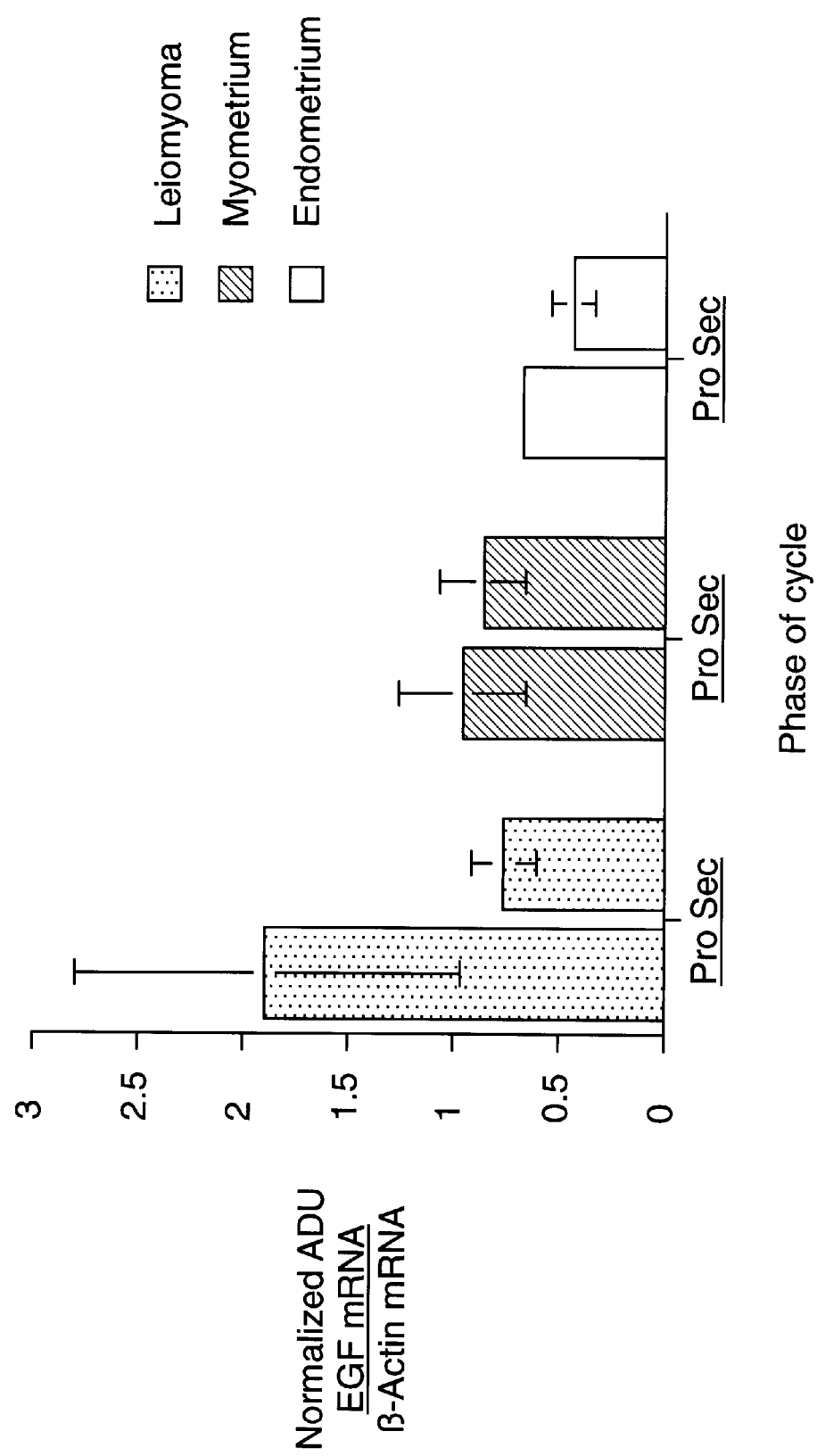

Elevated levels of EGF mRNA have been measured in leiomyomas previously and a role for EGF in stimulating growth and proliferation of leiomyomas has been proposed (26). In the instant experiments, differences in the levels of EGF mRNA in leiomyoma compared to myometrium (FIG. 7) were measured. The levels of EGF mRNA demonstrated a trend towards higher levels in leiomyoma from proliferative phase compared to leiomyoma collected during the secretory stage (P=0.08). However, there was no difference in EGF mRNA between leiomyoma and myometrium during either proliferative or secretory phase of the menstrual cycle.

Discussion

The results of these experiments reflect three important findings: (1) an increased level of stromelysin-2 and stromelysin-3 mRNA expression in leiomyoma relative to myometrium; (2) the presence of matrilysin mRNA in leiomyoma and myometrium; and (3) the absence of any apparent increase in either TIMP-1 or TIMP-2 mRNA levels associated with elevated metalloproteinases. These findings provide evidence for a role of selective up-regulation of metalloproteinases in leiomyoma compared to unaffected myometrium.

Uterine leiomyomas are benign tumors that grow rapidly, but do not escape from the connective tissue barrier that separates them from the myometrium. The potential for rapid growth of leiomyomas has been demonstrated previously (4, 17). The rapid growth of leiomyomas is in contrast to the relatively low mitotic rate of leiomyoma, which is similar to the unaffected myometrium (1). Although rapid tumor growth occurs in both benign and metastatic tumors, benign tumors such as leiomyomas are fibrotic tumors that rarely escape the basement membrane and metastasize (leiomyosarcoma). Furthermore, recent studies have found higher levels of collagen I, collagen III, and connexin in leiomyoma compared to myometrium (Nowak, unpublished results, 27). Collectively, results from recent studies suggest that leiomyomas possess a relatively low proliferation rate, but an active extracellular matrix environment. In the absence of elevated levels of collagenase in leiomyoma versus myometrium, relative to cell proliferation, leiomyoma cells are restricted in their infiltration of the surrounding myometrium or peripheral sites. The continued cell proliferation within the leiomyoma may exert force on the connective tissue boundary that invokes expansion, but not invasion.

In contrast to benign tumors, cells from invasive tumors have been shown to proliferate rapidly and either express elevated levels of metalloproteinases or induce expression of the enzymes from surrounding stromal cells (28). Cells from fibrosarcomas, choriocarcinomas and glioblastomas have been shown to produce gelatinases (29–31). Cells from metastatic colorectal and prostatic cancers (epithelial-derived) have been shown to produce matrilysin, and inhibition of matrilysin production from invasive cancer cells has been shown to decrease invasiveness (32–35). A high proportion (>95%) of invasive and metastatic breast cancers induce stromelysin-3 expression from surrounding stromal cells, whereas stromal cells surrounding non-invasive, non-metastatic breast cancers rarely express stromelysin-3 (36, 37). A common element among these invasive tumors is the juxtaposition of tumor cells with stromal cells prior to metastatic invasion. In contrast to invasive cancer, leiomyomas do not invade the surrounding tissue, and leiomyoma sequestered within the myometrium are not in contact with the uterine stroma.

The metalloproteinases are a family of enzymes that have been subdivided into three general categories based on their structure and substrate specificity. The structure, function and roles of collagenases, gelatinases and stromelysins in extracellular matrix remodeling and the substrates the various enzymes degrade have been reviewed recently (38–41). Briefly, the substrate of collagenases (MMP-1, MMP-8) has been shown to be interstitial collagens (collagen I, III) that form a structural framework of the extracellular matrix. Gelatinases have been shown to degrade denatured, non-helical domain collagen (collagen IV), adhesion proteins, and proteoglycans that form basement membranes. Stromelysins 1 and 2 are 80% identical and 89% similar at the amino acid level, and have been described to have similar enzymatic activity towards collagen IV, proteoglycans and matrix glycoproteins (42). A separate class of substrates preferentially cleaved by stromelysin-2 has not yet been identified. Stromelysin-3 has been shown to proteolyze $\alpha$1-antitrypsin, a serine protease inhibitor (serpin) and to date, this is the only characterized substrate for stromelsyin 3 (43). Matrilysin has also been shown to degrade $\alpha$1-antitrypsin, as well as collagen IV, fibronectin and laminin (44–46). These reported substrate preferences of stromelysin-2 and stromelysin-3 suggest that adhesion proteins and glycoproteins within the extracellular matrix are remodeled more extensively in leiomyoma compared to myometrium. These substrate preferences also suggest that components of the basement membrane and fibrillar collagen that are cleaved by stromelysin-1, collagenase, and gelatinases turnover less in leiomyoma compared to normal myometrium, and contribute to the dense fibrotic nature of the tumors.

The uterus is unique among adult organs with regard to the level of breakdown and remodeling of cells and extracellular matrix that occurs. A number of studies have examined the expression of metalloproteinases in the endometrium (12–14), and have demonstrated a remarkable increase in metalloproteinase expression coincident with growth and remodeling of the tissue. However, little information is available on the role of metalloproteinases in myometrium. The instant experiments are the first to demonstrate the presence and amounts of stromelysin-1, 2, and 3 and matrilysin mRNA in leiomyoma or myometrium, and the first to demonstrate elevated levels of stromelysin-2 and stromelysin-3 mRNA in leiomyoma compared to normal myometrium.

Prior to the instant experiments, stromelysin-3 and matrilysin were thought to be found exclusively associated with stromal cells and epithelial cells in the endometrium. Recently, stromelysin-3 has been found associated with myofibroblasts, a specialized type of stromal cell, and in dermatofibromas, a fibrotic tumor with a phenotype similar to leiomyoma (47). Although the subject experiments have not yet identified which cell types are involved in production of metalloproteinases, the myometrium also contains myofibroblasts that may be the potential source for stromelysin-3 production during growth and development of leiomyoma. Other cell types within the myometrium have also been shown to produce other proteases in other systems, and these cell types have the potential to produce metalloproteinases.

Mast cells within the uterus have been shown to produce at least two proteolytic enzymes, tryptase and chymase (48). The mast cell phenotype, characterized by production of tryptase or tryptase together with chymase, has been shown to be influenced by the tissue in which the mast cells reside. It is not known if mast cells directly or indirectly affect expression of metalloproteinases in the uterus. Other inflammatory cell types also present in the uterus such as neutrophils, monocytes and macrophages, have been shown to be sources of metalloproteinases (49–54). Therefore, there is potential for inflammatory cells to assume a unique phenotype within the myometrium or leiomyoma, and secrete metalloproteinases. Although the development of leiomyoma has been shown to be linked to chromosomal abnormalities (55, 56), an inflammatory component may be involved in the progression of the tumors.

The source of elevated stromelysin-2 and stromelysin-3 in leiomyoma remains currently in question, however, the presence of increased levels of enzyme could provide a proteolytically more active extracellular matrix compared to myometrium. A cascade of metalloproteinase activation involving stromelysin-2 and stromelysin-3 could also increase trypsin activity by proteolysis of $\alpha$1-antitrypsin, the only known substrate of stromelysin-3 (43). Combined with elevated trypsin-like activity, increases in selective matrix metalloproteinases may lead to expansion of the tumor, within the confines of the myometrium. Although these are hypothetical explanations for the involvement of matrix metalloproteinases in leiomyoma growth, the precise mechanisms responsible for rapid growth, matrix deposition and remodeling of leiomyomas without infiltration beyond the basement membrane are presently unknown.

In the subject experiments, expression of matrilysin mRNA was shown in leiomyoma and myometrium. Previous studies have shown matrilysin to be expressed predominantly in the epithelium of the endometrium (12, 13, 57). In support of matrilysin's being expressed in uterine tissues other than endometrial epithelium, other investigators (58) found that in patients with endometriosis, matrilysin was expressed in stromal layers of both eutopic and ectopic endometrium. (During endometrial biopsies, as conducted by the laboratories mentioned above, the myometrium was either not obtained during biopsy or matrilysin expression was not measured in the myometrium.) Matrilysin has been shown to be unique among metalloproteinases described thus far in that it lacks a C-terminal vitronectin-like domain, important for MMP attachment to matrix components (59, 60). Due to the unique structure of matrilysin, it has been proposed that matrilysin may represent the first member of a new sub-family of MMP's (61), and its expression in tissue types may vary in the presence of diseases such as endometriosis and uterine leiomyomas.

Endogenous tissue inhibitors of metalloproteinases (TIMP's) are often produced either by the same cells that produce metalloproteinases or by adjacent cells. The presence and activity of TIMP's in the uterus have been reported previously (62–64). In the subject experiments, there was a trend towards decreased TIMP-2 levels in leiomyoma compared to myometrium during the secretory phase but not during the proliferative phase. It is possible that decreased expression of TIMP-2 during the secretory phase, in the presence of increasing levels of stromelysin-2 and 3 mRNA expression, may provide greater opportunity for remodeling of leiomyoma compared to myometrium. The levels of TIMP-1 in stromal cells were similar throughout the menstrual cycle, but expression of TIMP-1 in epithelial layers demonstrated a more cyclic pattern (13). TIMP-1 mRNA levels were greatest during the menstrual phase of the cycle, coincident with the highest levels of several metalloproteinases during the most active time of uterine remodeling. TIMP's have been shown to inhibit metalloproteinases by preventing conversion of gelatinases from latent to active enzymes (65), and second, by inhibiting the N-terminal catalytic domain of matrix metalloproteinases in a noncovalent complex (66, 67). The metalloproteinase inhibition has been demonstrated in vitro and in vivo. TIMP has been shown to inhibit migration and invasion of some cancer cells (19–21, 68), but elevated levels of TIMP's have also been shown not to inhibit invasion of other cancer cells (69–71). In arthritic models, anti-inflammatory agents that reduce MMP expression have been shown to also increase levels of TIMP, restoring the balance between levels of MMP's and TIMP's in the joint (17, 72, 73). Recent studies have identified another TIMP, TIMP-3 (64), but the relative importance of TIMP-1, TIMP-2 or TIMP-3 in leiomyoma or myometrium are unknown.

In conjunction with elevated metalloproteinase activity, elevated EGF levels in leiomyoma were determined as compared to myometrium, consistent with previous reports concerning EGF and other growth factors shown to be elevated in leiomyoma. In the subject experiments, elevated levels of EGF mRNA were measured during the proliferative phase of the menstrual cycle, while previous reports show elevated levels of EGF mRNA measured during the secretory phase (26). Both the subject and previous experiments show elevated levels of EGF mRNA in leiomyoma, the reasons for the difference in results as related to the menstrual cycle (26) being unknown. A close correlation between the effects of estrogen and EGF on uterine growth has suggested that EGF may function as a modifier of estrogen action (74–76). However, elevated progesterone levels, but not elevated estrogen levels, correlate with a higher mitotic rate in leiomyomas (77, 78), suggesting that growth of cells and expansion of matrix may be elevated during the secretory phase of the cycle. In addition to EGF, other growth factors known to be associated with the heparin-rich extracellular matrix such as basic fibroblast growth factor and heparin-binding-epidermal growth factor, have also been shown to be elevated in leiomyoma relative to myometrium (79). The exclusive roles of estrogen and progesterone on leiomyoma growth have been difficult to separate. In addition, the precise roles of EGF and other growth factors contained in the extracellular matrix on the growth and mitotic rate of leiomyomas are presently unclear.

The levels of metalloproteinases have been reported to be elevated in many physiological conditions and diseases that involve tissue remodeling. Leiomyomas are a unique disease in which there is rapid growth and expansion of extracellular matrix within the boundaries of the growing tumor of mesenchymal origin. The experiments discussed herein provide evidence that a subset of matrix metalloproteinases, i.e., stromelysin-2 and stromelysin-3, are elevated in the leiomyoma compared to the myometrium. The physical nature of the leiomyomas further suggests that these enzymes, in the absence of elevated collagenase and stromelysin-1, may have a role in the development of the fibrotic phenotype of the tumor.

REFERENCES

1. Norris H. J. and Zaloudek C. J., 1977. Mesenchymal tumors of the uterus. In: Pathology of the Female Genital Tract, pp 352–392. Blaustein A., ed. Springer Verlag, New York, N.Y.
2. Friedman A. J., Barbieri R. L., Benacerraf B. R., and Schiff I., 1987. Treatment of leiomyomata with intranasal or subcutaneous leuprolide, a gonadotropin-releasing hormone agonist. Fert. Steril. 48: 560–565.
3. Friedman A. J., Hoffman D. I., Comite F., Browneller R. W., Miller J. D., 1991. Treatment of leiomyomata uteri with leuprolide acetate depot: A double-blind, placebo-controlled, multicenter study. Obstet. Gynecol. 77: 720–725.
4. Andreyko J. L., Blumenfeld Z., Marshall L. A., Monroe S. E., Hricak H. and Jaffe R. B., 1988. Use of an agonistic analog of gonadotropin-releasing hormone (nafarelin) to treat leiomyomas: Assessment by magnetic resonance imaging. Am. J. Obstet. Gynecol. 158: 903–910.
5. Murphy A. A., Kettel L. M., Morales A. J., Roberts V. J. and Yen S. C., 1993. Regression of uterine leiomyomata in response to the antiprogesterone RU-486. J. Clin. Endocrinol. Metab. 76: 513–517.
6. Townsend D. E., Sparkes R. S., Baluda M. C., and McClelland G., 1970. Unicellular histogenesis of uterine leiomyomas as determined by electrophoresis of glucose-6-phosphate dehydrogenase. Am. J. Obstet. Gynecol. 107: 1168–1173.
7. Vogelstein B., Fearon E. R., Hamilton S. R. and Feiberg A. P., 1985. Use of restriction fragment length polymorphisms to determine the clonal origin of human tumors. Science 227: 642–645.
8. Hashimoto K., Azuma C., Kamiura S., Kimura T., Nobunaga T., Kanai T., Sawada M., Noguchi S., Saji F., 1995. Clonal determination of uterine leiomyomas by analyzing differential inactivation of the X-chromosome-linked phosphoglycerokinase gene. Gynecol. Obstet. Invest. 40: 204–208.
9. Felmingham J. E. and Corcoran R., 1975. Comment: Rapid enlargement of a uterine fibroid after clomiphene therapy. Brit. J. Cbstet. Gynaecol. 82: 431–432.
10. Dilts P. V. Jr., Hopkins M. P., Chang A. E. and Cody R. L., 1992. Rapid growth of eicmyoma in patient receiving tamoxifen. Am. J. Cbstet. Gynecol. 166: 167–168.
11. Puistola U., Risteli L., Risteli J. and Kauppila A., 1990. Collagen metabolism in gynecologic patients: Changes in the concentration of the aminoterminal propeptide of type III procollagen in serum. Am J Obstet Gynecol 163: 1276–1281.
12. Rodgers W. H., Osteen K. G., Matrisian L. M., Navre M., Guidice L. C. and Gorstein F., 1993. Expression and localization of matrilysin, a matrix metalloproteinase, in human endometrium during the reproductive cycle. Am. J. Obstet. Gynecol. 168: 253–260.
13. Rodgers W. H., Matrisian L. M., Guidice L. C., Dsupin B., Cannon P., Svitek C., Gorstein F. and Osteen K. G., 1994. Patterns of matrix metalloproteinase expression in cycling endometrium imply differential functions and regulation by steroid hormones. J. Clin. Invest. 94: 946–953.
14. Schatz F., Papp C., Toth-Pal E. and Lockwood C. J., 1994. Ovarian steroid-modulated stromelysin-1 expression in human endometrial stromal and decidual cells. J. Clin. Endocrinol. Metab. 78: 1467–1472.
15. Harrison-Woolrych M. and Robinson R., 1995. Fibroid growth in response to high-dose progestogen. Fertil. Steril. 64: 191–192.
16. Murphy A. A., Morales A. J., Kettel L. M. and Yen S. S. C., 1995. Regression of uterine leiomyomata to the antiprogesterone RU486: dose-response effect. Fertil. Steril. 64: 187–190.
17. MacNaul K. L., Chartrain N., Lark M., Tocci M. J. and Hutchinson N. I., 1990. Discoordinate expression of stromelysin, collagenase, and tissue inhibitor of metalloproteinases-1 in rheumatoid human synovial fibroblasts. J. Biol. Chem. 265: 17238–17245.
18. Hembry R. M., Bagga M. R., Reynolds J. J. and Hamblen D. L., 1995. Immunolocalization studies on six matrix metalloproteinases and their inhibitors, TIMP-1 and TIMP-2, in synovia from patients with osteo- and rheumatoid arthritis. Ann. Rheum. Dis. 54: 25–32.
19. DeClerck Y. A., Yean, T. D., Chan D., Shimada H., Langley K. E., 1991. Inhibition of tumor invasion of smooth muscle cell layers by recombinant human metalloproteinase inhibitor. Cancer Res. 51: 2151–2157.
20. DeClerck Y. A., Perez N., Shimada H., Boone T. C., Langley K. E., Taylor S. M., 1992. Inhibition of invasion and metastasis in cells transfected with an inhibitor of metalloproteinases. Cancer Res. 52: 701–708.
21. Stearns M. E., Wang M., Stearns M., 1995. IL-10 blocks collagen IV invasion by "invasion stimulating factor" activated PC-3 ML cells: upregulation of TIMP-1 expression. Oncol. Res. 7: 157–163.
22. Hampton A. L. and Salamonsen L. A., 1994. Expression of messenger ribonucleic acid encoding matrix metalloproteinases and their tissue inhibitors is related to menstruation. J. Endocrinol. 141: R1–R3.
23. Chirgwin J. M., Przbyla A. E., MacDonald R. J., Rutter W. J., 1979. Isolation of biologically active ribonucleic acid from sources enriched in ribonucleases. Biochem. 18: 5294–5300.
24. Nowak R. A., Rein M. S., Heffner L. J., Friedman A. J. and Tashjian A. H., Jr., 1993. Production of prolactin by smooth muscle cells cultured from human uterine fibroid tumors. J. Clin. Endocrinol. Metab. 76: 1308–1313.
25. Nuovo G. J., MacConnell P. B., Simsir A., Valea F. and French D. L., 1995. Correlation of the in situ detection of polymerase chain reaction-amplified metalloproteinase complementary DNA's and their inhibitors with prognosis in cervical carcinoma. Cancer Research 55: 267–275.
26. Harrison-Woolrych M. L., Charnock-Jones, D. S. and Smith S. K., 1994. Quantification of messenger ribonucleic acid for epidermal growth factor in human myometrium and leiomyomata using reverse transcriptase polymerase chain reaction. J. Clin. Endocrinol. Metab. 78: 1179–1184.
27. Anderson J., Grine E. A., Eng C. L.-Y., Zhao K., Barbieri R. L., Chumas J. and Brink P. Expression of connexin-43 in human myometrium and leiomyomas. Am. J. Obstet. Gynecol. 169: 1266–1276.
28. Liotta L. A. and Stetler-Stevenson W. G., 1991. Tumor invasion and metastasis: An imbalance of positive and negative regulation. Cancer Research 51: 5054s–5059s.
29. Kato N., Nawa A., Tamakoshi K., Kikkawa F., Suganuma N., Okamoto T., Goto S., Tomoda Y., Hamaguchi M. and Nakajima M., 1995. Suppression of gelatinase production with decreased invasiveness of choriocarcinoma cells by recombinant interferon beta. Am. J. Obstet. Gynecol. 172: 601–606.
30. Rao J. S., Yamamoto M., Mohaman S., Gokaslan Z. L., Fuller G. N., Stetler-Stevenson W. G., Rao V. H., Liotta L. A., Nicolson G. L. and Sawaya R. E., 1995. Expression and localization of 92 kDa type IV collagnease/gelatinase B (MMP-9) in human gliomas. Clin. Exp. Metastasis 14: 12–18.
31. Okada Y., Gonoji Y., Naka K., Tomita K., Nakanishi I., Iwata K., Yamashita K. and Hayakawa T., 1992. Matrix metalloproteinase 9 (92-kDa gelatinase/type IV collagenase) from HT 1080 fibrosarcoma cells. J. Biol. Chem. 267: 21712–21719.
32. Kazushi I., Yokohama Y., Nakanishi I., Ohuchi E., Fujii Y., Nakai N. and Okada Y., 1995. Matrix metalloprotein- 32. ase 7 (matrilysin) from human rectal carcinoma cells. J. Biol. Chem. 270: 6691–6697.
33. Witty J. P., McDonnell S., Newell K. J., Cannon P., Navre M., Tressler R. J. and Matrisian L. M., 1994. Modulation of matrilysin levels in colon carcinoma cell lines affects tumorigenicity in vivo. Cancer Res. 54: 4805–4812.
34. Yamamoto H., Itoh F., Hinoda Y. and Imai K., 1995. Suppression of matrilysin inhibits colon cancer cell invasion in vitro. Int. J. Cancer 61: 218–222.
35. McDonnell S., Navre M., Coffey R. J. and Matrisian L. M., 1991. Expression and localization of the matrix metalloproteinase Pump-1 (MMP-7) in human gastric and colon carcinomas. Molec. Carcinog. 4: 527–533.
36. Basset P., Bellocq J. P., Wolf C., Stoll I., Hutin P., Limacher J. M., Podhajcer, Chenard M. P., Rio M. C. and Chambon P., 1990. A novel metalloproteinase gene specifically expressed in stromal cells of breast carcinomas. Nature 348: 699–704.
37. Wolf C., Rouyer N., Lutz Y., Adida C., Loriot M., Bellocq J.-P., Chambon P. and Basset P., 1993. Stromelysin-3 belongs to a subgroup of proteinases expressed in breast carcinoma fibroblastic cells is possibly implicated in tumor progression. Proc. Natl. Acad. Sci. USA 90: 1843–1847.
38. Salamonsen L. A., 1996. Matrix metalloproteinases and their tissue inhibitors in endocrinology. Trends in Endocrinol. Metab. 7: 28–34.
39. Cockett M. I., Birch M. L., Murphy G., Hart I. R. and Docherty A. J. P., 1994. Metalloproteinase domain structure, cellular invasion and metastasis. Bioch. Soc. Transact. 22: 55–57.
40. McDonnell S., Wright J. H., Gaire M., and Matrisian L. M., 1994. Expression and regulation of stromelysin and matrilysin by growth factors and oncogenes. Bioch. Soc. Transact. 22: 58–63.
41. Rucklidge G. J., Edvardsen K. and Bock E., 1994. Cell-adhesion molecules and metalloproteinases: a linked role in tumor cell invasiveness. Bioch. Soc. Transact. 22: 63–68.
42. Nagase H., 1995. Human stromelysins 1 and 2. In: Methods Enzymol. 248: 449–470. Ed. Alan J. Barret, Academic Press, Inc., New York, N.Y.
43. Pei D., Majmudar G. and Weiss S. J., 1994. Hydrolytic inactivation of a breast carcinoma cell-derived serpin by human stromelysin-3. J. Biol. Chem. 269: 25849–25855.
44. Sires U. I., Murphy G., Baragi V. M., Fliszar C. J., Welgus H. G. and Senior R. M., 1994. Matrilysin is much more efficient than other matrix metalloproteinases in the proteolytic inactivation of $\alpha$1-antitrypsin. Bioc. Biophys. Res. Comm. 204: 613–620.
45. von Bredow D. C., Nagle R. B., Bowden G. T., Cress A. E., 1995. Degradation of fibronectin fibrils by matrilysin and characterization of the degradation products. Exp. Cell Res. 221: 83–91.
46. Wilson C. L., Matrisian L. M., 1996. Matrilysin: an epithelial matrix metalloproteinase with potentially novel functions. Int. J. Biochem. Cell Biol. 28: 123–136.
47. Unden A. B., Sandstedt B., Bruce K., Hedblad M.-A. and Stahle-Backdahl M.-S., 1996. Stromelysin-3 mRNA associated with myofibroblasts is overexpressed in aggressive basal cell carcinoma and in dermatofibroma but not in dermatofibrosarcoma. J. Invest. Dermatol 107: 147–153.
48. Jeziorska M., Salamonsen L. A. and Woolley D. E., 1995. Mast cell and eosinophil distribution and activation in human endometrium throughout the menstrual cycle. Biol. Reprod. 53: 312–320.
49. Busiek D. F., Ross F. P., McDonnell S., Murphy G., Matrisian M., Welgus H. G., 1992. The matrix metalloprotease matrilysin (PUMP) is expressed in developing human mononuclear phagocytes. J. Biol. Chem. 267: 9087–9092.
50. Malik N., Greenfield B. W., Wahl A. F. and Kiener P. A., 1996. Activation of human monocytes through CD40 induces matrix metalloproteinases. J. Immunol. 156: 3952–3960.
51. Lee E., Grodzinsky A. J., Libby P., Clinton S. K., Lark M. W., Lee R. T., 1995. Human vascular smooth muscle cell-monocyte interactions and metalloproteinase secretion in culture. Arterioscler. Thromb. Vasc. Biol. 15: 2284–2289.
52. Corcorna, M. L., Kibbey M. C., Kleinman H. K., Wahl L. M., 1995. Laminin SIKVAV peptide induction of monocyte/macrophage prostaglandin E2 and matrix metalloproteinases. J. Biol. Chem. 270: 10365–10368.
53. Maillard J. L., Favreau C., Reboud-Ravaux M., 1995. Role of monocyte/macrophage derived matrix metalloproteinases (gelatinases) in prolonged skin inflammation. Clin. Chim. Acta 233: 61–74.
54. Lacraz S., Isler P., Vey E., Welgus H. G., Dayer, J.-M., 1994. Direct contact between T lymphocytes and monocytes is a major pathway for induction of metalloproteinase expression. J. Biol. Chem. 269: 22027–22033.
55. Hennig Y., Wanschura S., Deichert U., Bartnitzke S., Bullerdiek J., 1996. Rearrangements of the high mobility group protein family genes and the molecular genetic origin of uterine leiomyomas and endometrial polyps. Mol. Hum. Reprod. 2: 277–283.
56. Fezjo, M. S., Yoon S.-J., Montgomery K., Rein M. S., Weremowicz S., Krauter K. S., Dorman T. E., Fletcher J. A., Mao J., Moir D. T., Kucherlapati R. S. and Morton C. C., 1995. Identification of a YAC spanning the translocation breakpoints in uterine leiomyomata, pulmonary chondroid hamartoma and lipoma: physical mapping of the 12q14–q15 breakpoint region in uterine leiomyomata. Genomics 26: 265–271.
57. Osteen K. G., Rodgers W. H., Gaire M., Hargrove J. T., Gorstein F. and Matirisian L. M., 1994. Stromal-epithelial interaction mediates steroidal regulation of metalloproteinase expression in human endometrium. Proc. Natl. Acad. Sci. USA 91: 10129–10133.
58. Osteen K. G., Bruner K. L., Sierra-Rivera E., Keller N. R., Eisenberg E., 1996. Interleukin 1a opposes progesterone suppression of matrix metalloproteinases in an endometriosis model. Biol. Reprod. 54 (Suppl): 259.
59. Brooks, P. C., Stromblad S., Sanders L. C., von Schalscha T. L., Aimes R. T., Stetler-Stevenson W. G., Quigley J. P., Cheresh D. A., 1996. Localization of matrix metalloproteinase MMP-2 to the surface of invasive cells by interaction with integrin avb3. Cell 85: 683–693.
60. Xia M., Sreedharan S. P., Dazin P., Damsky C. H., Goetzel E. J., 1996. Integrin-dependent role of human T cell matrix metalloproteinasd activity in chemotaxis through a model basement membrane. J. Cell. Biochem. 61: 452–458.
61. Gaire M., Magbanua Z., McDonnell, McNeil L., Lovett and Matrisian L. M., 1994. Structure and expression of the human gene for the matrix metalloproteinase matrilysin. J. Biol. Chem. 269: 2032–2040.
62. Hara T., Tanaka S., Sato H., Seiki M., Tojo H., Tachi C., 1995. Expression of matrix metalloproteinase-11 (stromelysin-3) and TIMP-1 genes in the placenta and the uterus during estrous cycles and gestation in the mouse. J. Reprod. Dev. 41: 287–292.

63. Hosono T., Ito A., Sato T., Nagase H. and Mori Y., 1996. Translational augmentation of pro-matrix metalloproteinase 3 (prostromelysin-1) and tissue inhibitor of metalloproteinases (TIMP)-1 mRNAs induced by epidermal growth factor in human uterine cervical fibroblasts. FEBS Lett. 381: 115–118.
64. Reponen P., Leivo I., Sahlberg C., Apte S. S., Olsen B. R., Thesleff I. and Tryggvason K., 1995. 92-kDa type IV collagenase and TIMP-3, but not 72-kDa type IV collagenase or TIMP-1 or TIMP-2, are highly expressed during mouse embryo implantation. Dev. Dyn. 202: 388–396.
65. Strongin A. Y., Marmer B. L., Grant G. A. and Goldberg G. I., 1993. Plasma membrane-dependent activation of the 72-kDa Type IV collagenase is prevented by complex formation with TIMP-2. J. Biol. Chem. 268: 14033–14039.
66. Cawston T. E., Murphy G., Mercer E., Galloway W. A., Hazleman B. L. and Reynolds J. J., 1983. The interaction of purified rabbit bone collagenase with purified rabbit bone metalloproteinase inhibitor. Biochem J. 211: 313–318.
67. Murphy G., Koklitis P. and Carne A. F., 1989. Dissociation of tissue inhibitor of metalloproteinases (TIMP) from enzyme complexes yields fully active inhibitor. Biochem J. 261: 1031–1034.
68. Imren S., Kohn D. B., Shimada H., Blavier L., DeClerck Y. A., 1996. Overexpression of tissue inhibitor of metalloproteinases-2 by retroviral-mediated gene transfer in vivo inhibits tumor growth and invasion. Cancer Res. 56: 2891–2895.
69. Grignon D. J., Sakr W., Toth M., Ravery V., Angulo J., Shamsa F., Pontes J. E., Crissman J. C., Fridman, R., 1996. High levels of tissue inhibitor of metalloproteinase-2 (TIMP-2) expression are associated with poor outcome in invasive bladder cancer. Cancer Res. 56: 1654–1659.
70. Zeng Z.-S., Cohen A. M., Zhang Z.-F., Stetler-Stevenson W., Guillem J. G., 1995. Elevated tissue inhibitor of metalloproteinase 1 RNA in colorectal cancer stroma correlates with lymph node and distant metastases. Clin. Cancer Res. 1: 899–906.
71. Visscher D. W., Hoyhtya M., Ottosen S. K., Liang C.-M., Sarkar F. H., Crissman J. D., Fridman R., 1994. Enhanced expression of tissue inhibitor of metalloproteinase-2 (TIMP-2) in the stroma of breast carcinomas correlates with tumor recurrence. Int. J. Cancer 59: 339–344.
72. Dean D. D., Martel-Pelletier J., Pelletier J. P., Howell D. S. and Woessner J. F., Jr., 1989. Evidence for metalloproteinase and metalloproteinase inhibitor imbalance in human osteoarthritic cartilage. J. Clin. Invest. 84: 678–685.
73. McGuire M. B., Murphy G., Reynolds J. J. and Russell R. G. G., 1981. Production of collagenase and inhibitor (TIMP) by normal, rheumatoid, and osteoarthritic synovium in vitro: effects of hydrocortisone and indomethacin. Clin. Sci. 61: 703–710.
74. Ignar-Trowbridge D. M., Nelson K. G., Bidwell M. C., Curtis S. W., Washburn T. F., McLachlan J. A. and Korach K. S., 1992. Coupling of dual signaling pathways: epidermal growth factor action involves the estrogen receptor. Proc. Natl. Acad. Sci. U.S.A. 89: 4658–4662.
75. Ignar-Trowbridge D. M., Teng C. T., Ross K. A., Parker M. G., Korach K. S. and McLachlan J. A., 1993. Peptide growth factors elicit estrogen receptor-dependent transcriptional activation of an estrogen-responsive element. Mol. Endocrinol. 7: 992–998.
76. Ignar-Trowbridge D. M., Pimentel M., Parker M. G., McLachlan J. A., Korach, K. S., 1996. Peptide growth factor cross-talk with the estrogen receptor requires the A/B domain and occurs independently of protein kinase C or estradiol. Endocrinol 137: 1735 –1744.
77. Tiltman A., 1985. The effect of progestins on the mitotic activity of uterine fibromas. Int. J. Gynecol. Pathol 4: 89–96.
78. Kawaguchi K., Fuji S., Konishi I., Nanbu Y., Nonogake H., Mori T., 1989. Mitotic activity in uterine leiomyomas during the menstrual cycle. Am. J. Obstet. Gynecol. 160: 637–641.
79. Mangrulkar R. S., Ono M., Ishikawa M., Takashima S., Klagsbrun M., Nowak R. A., 1995. Isolation and characterization of heparin-binding growth factors in human leiomyomas and normal myometrium. Biol. Reprod. 53: 636–46.
80. Knight C. G., Willebrock F., Murphy G., 1992. A novel coumarin-labelled peptide for sensitive continuous assays of the matrix metalloproteinases. FEBS 296, No. 3: 263–266.

What is claimed is:

1. A method of treating a subject suffering from a leiomyoma which comprises inhibiting at least one metallopreinase selected from the group consisting of stromelysin-2, stromelysin-3 and matrilysin.

2. A pharmaceutical composition for treating a subject suffering from a leiomyoma which comprises an agent which specifically inhibits at least one metalloproteinase selected from the group consisting of stromelysin-2, stromelysin-3 and matrilysin, and a pharmaceutically acceptable carrier wherein the composition comprises an imadazole hydroxyamate of the formula:

wherein $R_2$, X and Y are $CH_2CHMe_2$, H and Ph, respectively, and $R_1$ is $CH_2CHMe_2$ or $C-C_6H_{11}$.

3. The pharmaceutical composition of claim 2 which comprises a plurality of agents, each of which specifically inhibits at least one metalloproteinase selected from the group consisting of stromelysin-2, stromelysin-3 and matrilysin, and a pharmaceutically acceptable carrier.

4. The method of claim 1, wherein the subject is a human.

5. The method of claim 1, wherein the leiomyoma is a uterine leiomyoma.

6. The method of claim 1, wherein the agent specifically inhibits stromelysin-2.

7. The method of claim 1, wherein the agent specifically inhibits stromelysin-3.

8. The methods of claim 1, wherein the agent specifically inhibits matrilysin.

9. The method of claim 1, wherein the agent specifically inhibits stromelysin-2, stromelysin-3 and matrilysin.

10. The method of claim 1 wherein the method comprises the step of administering an imadazole hydroxyamate of the formula:

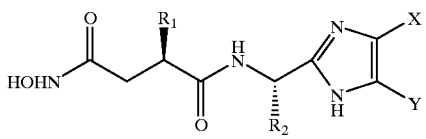

wherein $R_2$, X and Y are $CH_2CHMe_2$, H and Ph, respectively, and $R_1$ is $CH_2CHMe_2$ or $C—C_6H_{11}$.

11. The method of claim 10 wherein a plurality of agents, each of which specifically inhibits at least one metalloproteinase selected from the group consisting of stromelysin-2, stromelysin-3 and matrilysin is administered to the subject.

12. The method of claim 11, wherein the subject is a human.

13. The method of claim 11, wherein the leiomyoma is a uterine leiomyoma.

14. The method of claim 11, wherein the agent specifically inhibits stromelysin-2.

15. The method of claim 11, wherein the agent specifically inhibits stromelysin-3.

16. The method of claim 11, wherein the agent specifically inhibits matrilysin.

17. The method of claim 11, wherein the agent specifically inhibits stromelysin-2, stromelysin-3 and matrilysin.

18. The method of claim 1 wherein the method comprises the step of administering at least a portion of a matrix metalloproteinase inhibitor.

* * * * *